United States Patent [19]

Hatfield et al.

[11] 4,211,702
[45] Jul. 8, 1980

[54] PROCESS FOR PREPARATION OF PENICILLIN AND CEPHALOSPORIN IMINO HALIDES

[75] Inventors: Lowell D. Hatfield, Bargersville; Larry C. Blaszczak; Jack W. Fisher, both of Indianapolis, all of Ind.

[73] Assignee: Eli Lilly and Company, Indianapolis, Ind.

[21] Appl. No.: 8,470

[22] Filed: Feb. 1, 1979

[51] Int. Cl.$^2$ ............... C07D 499/10; C07D 501/02; C07D 265/12

[52] U.S. Cl. ............................ 260/239.1; 544/16; 544/17; 544/18; 544/19; 544/20; 544/21; 544/22; 544/23; 544/24; 544/25; 544/26; 544/27; 544/28; 544/29; 544/30; 544/90; 544/92

[58] Field of Search ............... 260/239.1; 544/16, 17, 544/18, 19, 20, 21, 22, 23, 24, 25, 26, 27, 28, 29, 30, 90, 92

[56] References Cited

U.S. PATENT DOCUMENTS

| | | | |
|---|---|---|---|
| 3,549,628 | 12/1970 | Chauvette | 544/20 |
| 3,575,970 | 4/1971 | Weissenburger et al. | 544/20 |
| 3,660,396 | 5/1972 | Wright | 260/239.1 |
| 3,669,980 | 6/1972 | Bogash et al. | 260/239.1 |
| 3,697,515 | 10/1972 | Fechtig et al. | 544/20 |
| 3,832,347 | 8/1974 | Kukolja et al. | 260/239.1 |
| 3,845,043 | 10/1974 | Hatfield | 260/239.1 |
| 3,868,368 | 2/1975 | Hatfield | 544/20 |
| 3,873,533 | 3/1975 | Bogash et al. | 260/239.1 |
| 3,875,146 | 4/1975 | Christensen et al. | 260/239.1 |
| 3,932,393 | 1/1976 | Chauvette | 544/16 |
| 3,932,465 | 1/1976 | Peter et al. | 544/16 |
| 3,954,732 | 5/1976 | Kamiya et al. | 260/239.1 |
| 4,008,229 | 2/1977 | Spitzer | 260/239.1 |
| 4,042,585 | 8/1977 | Koppel | 544/22 |
| 4,052,387 | 10/1977 | Kukolja | 544/22 |
| 4,058,610 | 11/1977 | Cox et al. | 544/26 |
| 4,060,688 | 11/1977 | Chauvette | 544/30 |
| 4,066,641 | 1/1978 | Hamashima et al. | 544/17 |

Primary Examiner—Natalie Trousof
Assistant Examiner—Vera C. Clarke
Attorney, Agent, or Firm—Steven R. Lammert; Arthur R. Whale

[57] ABSTRACT

Penicillin and cephalosporin imino halides are prepared by reacting of 6-acylaminopenicillins or 7-acylamino cephalosporins with a novel chlorinating compound derived from a triaryl phosphite and chlorine or bromine. The imino halide products are intermediates in the preparation of antibiotic compounds.

24 Claims, No Drawings

PROCESS FOR PREPARATION OF PENICILLIN AND CEPHALOSPORIN IMINO HALIDES

BACKGROUND AND SUMMARY OF THE INVENTION

In the preparation of semi-synthetic penicillin and cephalosporin antibiotics most chemical modifications are performed on β-lactam substrates bearing C-6 or C-7 acylamino groups which are stable to the process conditions but are not preferred for maximum antibiotic activity. Thus, a process step common to the production of most if not all of the known clinically significant penicillins and cephalosporins is the cleavage of the C-6 or C-7 acylamino group to provide the corresponding C-6 or C-7 amino compounds which are reacylated as desired. Undoubtedly the most widely used method for cleaving penicillin and cephalosporin acylamino side chains is that wherein the C-6 or C-7 acylamino compound is first converted to the corresponding imino halide and then to an imino ether which, upon acidic hydrolysis or alcoholysis, provides the nucleus (C-6 or C-7 amino) compounds. This general method and improvements thereof have been described in a number of U.S. Patents including Nos. 3,549,628, 3,575,970, 3,697,515, 3,845,043 and 3,868,368.

A number of acid halides, especially, acid chlorides, derived from phosphorus, carbon and sulfur or their oxygen acids have been disclosed as useful for preparing the imino halide intermediates of the three-step amido cleavage process. Phosphorus oxychloride, phosphorus pentachloride, phosphorus trichloride, thionyl chloride, phosgene, oxalyl chloride and catechyl-phosphorus trichloride have, in particular, been described as suitable imino halide forming reagents. Laboratory experience has shown phosphorus pentachloride to be a preferred acid halide reagent for intermediate imino halide preparation.

Recently we have discovered a novel class of halogenating compounds derived not from phosphorus oxygen acids but from aryl esters thereof. More specifically we have discovered that selected triaryl phosphites react with equivalent amounts of chlorine or bromine to provide, initially, kinetically controlled products which, although thermodynamically unstable, can be used advantageously in many halogenation reactions, including the preparation of penicillin and cephalosporin imino halides. These novel halogenating compounds are disclosed and claimed in our co-pending U.S. application Ser. No. 8,469 filed on even date herewith.

It is an object of the present invention to provide a new process for preparing penicillin and cephalosporin imino halides.

It is a more specific object of the present invention to provide a high yielding method of preparing C-6 or C-7 imino halides of penicillin and cephalosporin respectively using novel triaryl phosphite-halogen kinetic complexes.

DETAILED DESCRIPTION OF THE INVENTION

This invention is directed to a process for preparing penicillin or cephalosporin imino halides which comprises reacting a C-6 acylamino penicillin or a C-7 acylamino cephalosporin with about 1.0 to about 2.0 equivalents of a halogenating compound of the formula

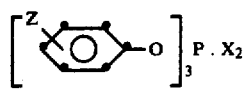

wherein X is Cl or Br, and Z is hydrogen, halo, $C_1$-$C_4$ alkyl or $C_1$-$C_4$ alkoxy, which is the kinetically controlled product of the reaction of equivalent amounts of a triaryl phosphite of the formula

and chlorine or bromine in a substantially anhydrous inert organic solvent, in the presence of about 1.0 to about 1.2 equivalents of a tertiary amine base per equivalent of halogenating compound employed, in a substantially anhydrous inert organic solvent at a temperature of about 30° or below, with the proviso that when the C-6 acylamino penicillin or C-7 acylamino cephalosporin is substituted by hydroxy, amino or carboxy groups those groups are first protected with conventional hydroxy, amino or carboxy protecting groups.

Triaryl phosphites of the formula

wherein Z is hydrogen, halo, $C_1$-$C_4$ alkyl or $C_1$-$C_4$ alkoxy, have been found to react with chlorine or bromine in a substantially anhydrous inert organic solvent to provide, initially, kinetically controlled products having the empirical formula

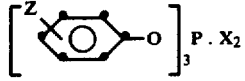

wherein Z is as defined above and X is Cl or Br.

The term "halo" in the definition of Z includes chloro, bromo or iodo. "$C_1$-$C_4$ alkyl" includes methyl, ethyl, isopropyl, n-propyl, n-butyl, sec-butyl, tert-butyl and isobutyl. Representative "$C_1$-$C_4$ alkoxy" groups are methoxy, ethoxy, isopropoxy, tert-butoxy and n-butoxy.

The dot (·) in the general formula used to represent the kinetically controlled products is used simply to designate that equivalent amounts of halogen and triaryl phosphite are combined chemically and in a way that can be distinguished from that in the thermodynamically stable derivatives which have been known in the art and which typically have been drawn without the dot [e.g. $(PhO)_3PCl_2$]. The exact molecular form of the triaryl phosphite-halogen kinetic complexes described herein has not been established definitively. However, physical-chemical data do indicate that the kinetic product is one wherein the phosphorus center acquires some cationic character. Herein the terms "kinetic compound", "kinetic complex", "triaryl phosphite-halogen complex (compound)" "kinetically controlled halogenating compound", and "kinetically controlled product" are used synonomously.

Suitable triarylphosphites for the preparation of the kinetically controlled halogenating compounds include triphenyl phosphite, tri(p-methoxyphenyl)phoshite, tri(o-chlorophenyl)phosphite, tri(p-chlorophenyl)phosphite, tri(p-tolyl)phosphite, tri(o-tolyl)phosphite, tri(m-bromophenyl)phosphite, tri(p-bromophenyl)phosphite, tri(p-iodophenyl)phosphite, tri(p-n-propylphenyl)phosphite, tri(p-tert-butylphenyl)phosphite, tri(m-tolyl)phosphite, tri(p-isopropoxyphenyl)phosphite and the like. Triphenyl phosphite is preferred.

Any of a wide variety of inert organic solvents may be employed as the medium for the preparation of the kinetically controlled halogenating compounds and for the halogenating process described hereinbelow. By "inert organic solvent" is meant an organic solvent, which under the reaction conditions of the preparation, does not enter into any appreciable reaction with either the reactants or the products. Since the halogenating compounds used in the present process are susceptible to reaction with protic compounds, such compounds, including water, alcohols, amines (other than tertiary), thiols, organic acids and other such protic compounds should be excluded from the reaction medium.

A substantially anhydrous aprotic organic solvent is preferred. The term "substantially anhydrous" as used in the present description means that although anhydrous organic solvents are generally preferred, trace amounts of water, such as that often found in commercially available solvents, can be tolerated. Although the kinetic products described herein will react with any water present in the solvent medium, additional amounts of reagents can easily be added to compensate for the lose due to hydrolysis. It is preferred that conventional laboratory techniques be employed to dry the solvents employed and to exclude moisture from the reaction mixtures.

Suitable solents include hydrocarbons, both aliphatic and aromatic, including pentane, hexane, heptane, octane, cyclohexane, cyclopentane, benzene, toluene, o-, m- or p- xylene, mesitylene and the like; ethers, cyclic and acyclic such as diethyl ether, butyl ethyl ether, tetrahydrofuran, dioxane, 1,2-dimethoxyethane and the like; carboxylic acid esters such as ethyl acetate, methylformate, methyl acetate, amyl acetate, n-butyl acetate, sec-butyl acetate, methyl propionate, methyl butyrate and the like; nitriles such as acetonitrile, propionitrile, butyronitrile and the like; halogenated hydrocarbons, both aromatic and aliphatic, such as chloroform, methylene chloride, carbon tetrachloride, 1,2-dichloroethane (ethylene dichloride), 1,1,2-trichloroethane, 1,1-dibromo-2-chloroethane, 2-chloropropane, 1-chlorobutane, chlorobenzene, fluorobenzene, o-, m-, or p- chlorotoluene, o-, m-, or p-bromotoluene, dichlorobenzene and the like; and nitro compounds such as nitromethane, nitroethane, 1- or 2-nitropropane, nitrobenzene and the like.

The particular inert organic solvent employed as a medium for the preparation of the kinetically controlled triaryl phosphite-halogen compounds or as a medium for their use in the present halogenation process is not critical. However, such solvent properties as polarity, melting or boiling point, and ease of isolation of halogenated products may be considered in selecting a most suitable solvent.

Preferred solvents for the preparation of the kinetically controlled products, that is, the halogenating compounds employed in the present process, and for the present process are hydrocarbons, especially aromatic hydrocarbons, and halogenated hydrocarbons.

If a halogenating compound derived from the kinetically controlled reaction of a triaryl phosphite and chlorine or bromine is allowed to stand in solution it converts or isomerizes to the corresponding thermodynamically stable compound at varying rates depending on, among other things, the nature of the triaryl phosphite, the halogen, the solvent and the solution temperature. Experimental data have also shown that the presence of an acid (HX) or an excess of triaryl phosphite will increase the rate of conversion of the kinetic to the thermodynamic product. Using $^{31}P$ nuclear magnetic resonance spectroscopy the half-life of the kinetically controlled product from the reaction of triphenyl phosphite and chlorine in methylene chloride at room temperature was determined to be about 8 hours. A half-life of about 39 hours was observed for the triphenyl phosphite-bromine kinetic complex under the same conditions. As mentioned above the observed half-life (rate of conversion) for any given kinetic complex described herein can be affected by the solvent and by the presence of a hydrogen halide acid (HX) or excess triaryl phosphite. Thus, for example, a shorter half-life will be observed where the solvent for the preparation of kinetic complex has not been rigorously dried; the hydrogen halide acid produced from reaction of the kinetic complex with the moisture present in the solvent will enhance the rate of conversion to the stable form.

Table I presents a summary of several properties of the kinetically controlled product and the corresponding thermodynamically controlled product of the reaction of triphenyl phosphite and chlorine.

Table I

| Kinetic product | Thermodynamic product |
|---|---|
| 1. $^{31}P$ nmr (CH$_2$Cl$_2$) − 3.7 ppm* | 1. $^{31}P$ nmr (CH$_2$Cl$_2$) + 22.7 ppm* |
| 2. $t_{\frac{1}{2}} = \approx 8$ hours at room temperature in methylene chloride | 2. Stable at room temperature |
| 3. ir (CH$_2$Cl$_2$) 1120–1190 (vs), 1070 (vs), 1035 (s), 1010 (vs), 990 (vs), 640 (m), 625 (m), 580 (w), 510 (s), 465 (w).** | 3. ir (CH$_2$Cl$_2$) 1130–1210 (vs), 1065 (vs), 1035 (s), 1010 (vs), 980 (vs), 625 (vw), 590 (m), 505 (s) 460 (s).** |
| 4. Hydrolyzes to give HCl and (PhO)$_3$PO | 4. Hydrolyzes to give inter alia HCl, PhOH (phenol) and (PhO)$_2$PCl |
| 5. Reacts with n-BuOH to give HCl, n-BuCl and PhO$_3$PO | 5. Reacts with n-BuOH to give HCl, PhOH (phenol), n-BuCl and (PhO)$_a$—(BuO)$_b$ POCl$_c$ wherein a,b,c, = 0, 1, 2 or 3 and a + b + c = 3 |

*Relative to $^-P$ of H$_3$PO$_4$; (+) indicates upfield shift; (−) indicates downfield shift.
**vs = very strong, s = strong, m = medium, w = weak The term kinetically controlled product is a term of art which when used in reference to reactions yielding two (or more) products, refers to the product formed faster, regardless of its thermodynamic stability. If such a reaction is stopped well before the products achieve thermodynamic equilibrium, the reaction is said to be kinetically controlled since more of the faster formed product will be present. In some cases, including the reaction of triaryl phosphites and chlorine or bromine in inert organic solvents, the rate of formation of the kinetic product and the rate of thermodynamic equilibrium are such that the kinetically controlled product can be prepared and utilized before any significant amount of the kinetically controlled product isomerizes to the thermodynamically stable product. To maximize the production and stability of the kinetically controlled product, reaction conditions are selected so as to minimize the potential for thermodynamic equilibrium of the initial product of the reaction. Conditions for kinetic control are achieved most simply by lowering the reaction temperature and the temperature of the kinetic product after it is formed, and by minimizing the time allowed for thermodynamic equilibrium, such as by utilizing the kinetic product in a subsequent reaction shortly after it has been prepared.

Typically the reactants, a triaryl phosphite and chlorine or bromine, are combined in a substantially anhydrous inert organic solvent at a temperature below about 30° C. Although the kinetically controlled products are formed at higher temperatures, such conditions favor more the formation of the thermodynamically controlled products. Preferably the halogenating compounds are prepared at temperatures at or below about 30° C. Minimum reaction temperatures are, of course, determined by the freezing point of the solvent employed for the preparation. Most preferred reaction temperatures are in the range of about −70° to about 0° C.

It has been found that the triaryl phosphite itself reacts to some extent with its kinetic product with chlorine or bromine, effectively increasing the rate of conversion to the corresponding thermodynamic product. It is preferred, therefore, but not required, that an excess of halogen be maintained in the reaction mixture during the formation of the halogenating compounds. This can be achieved practically by adding the triaryl phosphite to a solution of an equivalent amount of the halogen or by adding the halogen and the triaryl phosphite simultaneously to a quantity of inert organic solvent at the desired temperature. The co-addition of reagents is conducted at such a rate that the color of the halogen persists in the reaction mixture until the last drop of triaryl phosphite discharges the color. Alternatively excess halogen can be discharged using known halogen scavengers such as acetylenes, or olefins including alkenes, dienes, cycloalkenes, or bicycloalkenes. A preferred scavenger is a $C_2$ to $C_6$ alkene, for example, ethylene, propylene, butylene, or amylene.

The kinetically controlled halogenating reagents used in the process of the present invention are stabilized in solution by the addition of about 10 to about 100 mole percent of a tertiary amine base, preferably having a $pK_b$ value of about 6 to about 10. If, for example, about 50 mole percent of pyridine is added to a solution of the triphenyl phosphite and chlorine in methylene chloride, only trace amounts of the thermodynamic equilibrium product can be detected by $^{31}P$ nmr, even after prolonged periods at room temperature. The tertiary amine base can be added to a solution of the freshly prepared chlorinating compound or it can optionally be employed in the reaction mixture of the triarylphosphite and halogen to produce a stabilized solution of the kinetically controlled product used in the process of the present invention.

Triphenyl phosphite-halogen complexes (Z=H) are the preferred halogenating compounds in the present process. The triphenyl phosphite-chlorine kinetic complex is most preferred. About 1.0 to about 2.0 equivalents of halogenating compound are employed in the present process for each equivalent of penicillin or cephalosporin starting material. Best results are seen when about 1.1 to about 1.2 equivalents of halogenating compound are employed for each equivalent of penicillin or cephalosporin starting material.

C-7 Acylamino cephalosporin and C-6 acylamino penicillin starting materials for the present halogenating process are all known compounds, or they can be derived from known compounds by conventional procedures. The patent and chemical literature is replete with teachings of how to prepare penicillin and cephalosporin compounds which can be used in the present process. For example, 3-exomethylene cepham compounds are described in U.S. Pat. Nos. 3,932,393, 4,052,387 and 4,060,688. 2-Methyl-3-cephems are described in the *Journal of the American Chemical Society*, 97, 5020 (1975) and 98, 2342 (1976). Also the book *Penicillins and Cephalosporins*, E. H. Flynn, ed., Academic Press, New York, 1972, describes a wide variety of penicillins and cephalosporins and preparations thereof.

The starting materials for the present process can be represented by the general formula

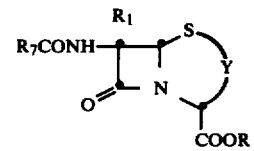

To the extent that there are no unprotected amino, hydroxy, carboxy groups or other protic substituents on these starting materials, the nature of the variables R, $R_1$, Y and $R_7$ is not critical to the present process. It is the C-6 or C-7 amido functionality which is modified under the conditions of the present process, from —CONH— to

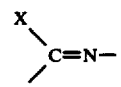

wherein X is chloro or bromo. R, $R_1$, $R_7$ and Y typically remain uneffected. Of course, as with most other chemical processes, yields of imino halide products or nucleus esters derived therefrom can vary from one substrate to another.

Representative of the starting materials which can be employed in the present process are those of the above formula wherein R is carboxylic acid protecting group;

$R_1$ is hydrogen or methoxy;

$R_7CO$— is an acyl group derived from a carboxylic acid; and

Y is a divalent radical selected from the group consisting of

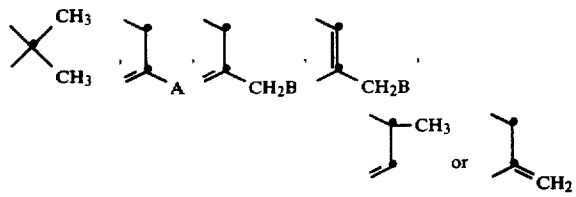

wherein

A is hydrogen, chloro, bromo, protected hydroxy, $C_1$-$C_4$ alkoxy, methyl, $C_1$-$C_4$ alkanesulfonyloxy or $C_1$-$C_4$ alkylphenylsulfonyloxy;

B is
(1) $C_2$-$C_4$ alkanoyl, carbamoyloxy, or $C_1$-$C_4$ alkylcarbamoyloxy;
(2) $C_1$-$C_4$ alkoxy;
(3) chloro or bromo;
(4) a group of the formula -$SR_9$ wherein $R_9$ is
  (a) $C_1$-$C_4$ alkanoyl;
  (b) $C_1$-$C_4$ alkyl, phenyl or phenyl substituted with 1 or 2 substituents selected from the group consisting of $C_1$-$C_4$ alkyl, $C_1$-$C_4$ alkoxy, protected hydroxy, chloro, bromo, fluoro, nitro, cyano, methanesulfonamido and trifluoromethyl; or
  (c) a 5- or 6-membered heterocyclic ring containing 1 to 4 heteroatoms selected from the group consisting of oxygen, sulfur and nitrogen, said ring being unsubstituted or substituted by $C_1$-$C_4$ alkyl, $C_1$-$C_4$ alkoxy, chloro, bromo, oxo, halo($C_1$-$C_4$ alkyl), protected amino, protected amino($C_1$-$C_4$ alkyl), protected hydroxy, protected hydroxy($C_1$-$C_4$ alkyl), protected carboxy, or protected carboxy ($C_1$-$C_4$)alkyl.

Alternatively the C-7 acylamino cephalosporin starting material for the present process can be a 1-oxadethiacephem compound of the formula

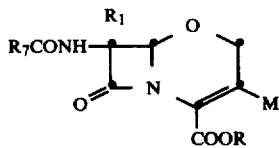

wherein R, $R_1$, and $R_7$ are as defined above and M is -A or —$CH_2B$ as defined above. These, too, are known compounds, or they can be derived from known compounds by conventional procedures. They, as well as the corresponding 1-carba-dethiacephems and 1-azadethiacephems which can also be employed in the present process, are described in Netherlands Patent Application No. 73/14711, and U.S. Pat. No. 4,123,528, issued Oct. 31, 1978. Other references describing the preparation of such compounds are:

L. D. Cama, B. G. Christensen, J. Amer. Chem. Soc., 96, 7582 (1974);

R. N. Guthikonda et. al., J. Amer. Chem. Soc., 96, 7584 (1974);

Saul Wolf et al., Can. J. Chem. 52, 3996 (1974);

R. A. Firestone et. al., J. Med. Chem. 20, 551 (1975); and

M. Narisada et. al., Heterocycles, 7 839 (1977).

Representative of $R_9$ when $R_9$ is an unsubstituted heterocyclic ring are pyridyl, pyrazinyl, pyridazinyl, pyrimidyl, 1,2,4-triazinyl, pyrazolyl, imidazolyl, thiazolyl, 1,2,4-triazolyl, 1,2,3-triazolyl, 1,2,3-thiadiazolyl, 1,2,4-thiadiazolyl, 1,3,4-thiadiazolyl, 1,2,3-oxadiazolyl, 1,2,4-oxadiazolyl, 1,3,4-oxadiazolyl, 1H-tetrazolyl, 2H-tetrazolyl and the like.

The carboxylic acids from which the C-7 substituents, $R_7$CONH—, are derived are typically $C_1$-$C_{20}$ carboxylic acids. A preferred group of C-7 acylamino substituents for the starting materials for the processes of the present invention are those conventional in the penicillin and cephalosporin art and includes, but are not limited to those described in U.S. Pat. Nos. 3,947,413; 3,932,465; 3,954,732; 3,660,396; 3,948,927; 4,052,387; 4,053,469; 4,058,610; 4,066,641 and 4,042,585. Because of the reactivity of the halogenating agent used in the present invention with protic functional groups, for example carboxy, amino and hydroxy groups, such functional groups if present on the C-7 side chain moiety of the substrate should first be protected using conventional carboxy, amino and hydroxy protecting groups. A non-limiting representation of C-6 or C-7 acylamino groups for the starting materials for the present processes are acylamino groups of the formula $R_7$CONH— wherein $R_7$ is (1) hydrogen, $C_1$-$C_6$ alkyl, halo($C_1$-$C_4$)alkyl, cyanomethyl, trifluoromethylthiomethyl, or 4-protected amino-4-protected carboxy butyl;

(2) the group $R_a$ wherein $R_a$ is phenyl or phenyl substituted with 1 or 2 substituent selected from the group consisting of $C_1$-$C_4$ alkyl, $C_1$-$C_4$ alkoxy, protected hydroxy, chloro, bromo, fluoro, iodo, nitro, cyano carbamyl, methanesulfonamido and trifluoromethyl;

(3) an arylalkyl group of the formula

wherein R° is $R_a$ as defined above, 1,4-cyclohexadienyl, or a 5-membered heterocyclic ring containing 1 to 4 heteroatoms selected from the group consisting of oxygen, nitrogen, and sulfur said ring being unsubstituted or substituted by $C_1$-$C_4$ alkyl, $C_1$-$C_4$ alkoxy, chloro, bromo, oxo, protected amino, protected amino($C_1$-$C_4$ alkyl), protected hydroxy or protected carboxy;

m is 1 or 0

Q is oxygen or sulfur, and $Q_1$ and $Q_2$ are independently hydrogen or methyl; subject to the limitation that in the above formula when m is 1, R° is limited to $R_a$; or (4) a substituted arylalkyl group of the formula

wherein R° is as defined above and W is protected amino, protected hydroxy or protected carboxy.

Exemplary of such acylamino groups are formamido, acetamido, propionamido, butyramido, chloroacetamido, 2-bromopropionamido, cyanoacetamido, trifluoromethylthioacetamido, 4-tert-butoxycarbonylamino-4-tert-butyoxycarbonylbutyramido, benzamido, 4-methylbenzamido, 3-nitrobenzamido, 2-iodobenzamido, 4-benzyloxybenzamido, 3-cyanobenzamido, 2,6-dichlorobenzamido, 4-trifluoromethylbenzamido, 3,4-diethoxybenzamido, 3-methanesulfonamidobenzamido.

When $R_7$ is a group R°-(Q)$_m$-$CQ_1Q_2$- representative acylamino groups are phenylacetamido, 4-bromophenylacetamido, 3,5-dinitrophenylacetamido, 4-benzyloxyphenylacetamido, phenoxyacetamido, 4-chlorophenoxyacetamido, 2-propoxyphenoxyacetamido, 4-carbamylphenoxyacetamido, cyclohexadienylacetamido, phenylthioacetamido, 2,5-dichlorophenylthioacetamido, 3-nitrophenylthioacetamido, 2-trifluoromethylphenylthioacetamido, 2-phenylproponamido, 2-phenoxypropionamido, 2-phenyl-2-methylpropionamido, 2-(4-chlorophenyl)propionamido, 2-furylacetamido, 2-thienylacetamido, 5-isooxazolylacetamido, 2-thiazolylacetamido, 2-thienylpropionamido, 5-thiazolylacetamido, 2-chloroacetamidothiazol-5-ylacetamido, 5-bromothien-2-ylacetamido, 1-tetrazolylacetamido, 5-tetrazolylacetamido and the like.

Illustrative of the acylamino groups when R7 is a substituted arylalkyl group of the formula

and when W is protected hydroxy are 2-formyloxy-2-phenylacetamido, 2-benzyloxy-2-(4-methoxyphenyl)acetamido, 2-(4-nitrobenzyloxy)-2-(3-chlorophenyl)acetamido, 2-chloroacetoxy-2-(4-methoxyphenyl)acetamido, 2-benzyloxy-2-phenylacetamido, 2-trimethylsilyloxy-2-(4-chlorophenyl)acetamido, 2-benzhydryloxy-2-phenylacetamido and like groups. Representative of such groups when W is protected amino are 2-(4-nitrobenzyloxycarbonylamino)-2-phenylacetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)acetamido, 2-benzhydryloxycarbonylamino-2-phenylacetamido, 2-(1-carbomethoxy-2-propenyl)amino-2-phenylacetamido, 2-(4-nitrobenzyloxycarbonylamino)-2-(2-thienyl)acetamido and like groups. Representative acylamino groups when W is protected carboxy are 2-(4-nitrobenzyloxycarbonyl)-2-(2-thienyl)acetamido, 2-benzhydryloxycarbonyl-2-phenylacetamido, 2-(2,2,2-trichloroethoxycarbonyl)-2-(4-chlorophenyl)acetamido, 2-(tert-butoxycarbonyl-2-(4-benzyloxyphenyl)acetamido and like groups.

The term "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, the 2,2,2-trichloroethoxycarbonyl group, or the 1-carbomethoxy-2-propenyl group formed with methyl acetoacetate. Like amino protecting groups such as those described by J. W. Barton in *Protective Groups in Organic Chemistry*, J. F. W. McOmie, Ed., Plenum Press, New York, N.Y., 1973, Chapter 2 shall be recognized as suitable. Conventional amino protecting groups that form a —CONH— function with the protected amino group can be chlorinated under the conditions of the present process and subsequently removed. If such reaction is desired, it can be accomplished by adding an additional equivalent of halogenating reagent and an alcohol to cleave the resulting imino halide.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in *Protective Groups in Organic Chemistry*, supra, Chapter 3 shall be considered as within the term "protected hydroxy" as used herein.

The term "carboxylic acid protecting group" has reference to the commonly used carboxylic acid protecting groups employed to block or protect the carboxylic acid functionality while reactions involving other functional sites of the compound are carried out. Such carboxy protecting groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, $C_2$-$C_6$ alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri($C_1$-$C_3$ alkyl)silyl, succinimidomethyl and like ester forming moieties. In addition to ester protection of carboxy groups, such groups can also be protected as the mixed anhydride, such as that formed with acetyl chloride, propionyl chloride, isobutyryl chloride and like acid chlorides in the presence of a tertiary amine base. Other known carboxy protecting groups such as those described by E. Haslam in *Protective Groups in Organic Chemistry*, supra, Chapter 5, shall be recognized as suitable. The nature of such ester forming groups is not critical.

In the foregoing definitions hydroxy, amino and carboxy protecting groups are not exhaustively defined. The function of such groups is to protect the reactive functional groups during the present process and then to be removed at some later point in time without disrupting the remainder of the molecule. Many protecting groups are known in the art, and the use of other protecting groups not specifically referred to hereinabove are equally applicable to the substrates of the process of the present invention.

The present imino halide forming process is conducted in the presence of a tertiary amine base. Suitable tertiary amine bases are those having a $pK_b$ value of about 1 to about 10. Preferred tertiary amine bases are those having a $pK_b$ value of about 6 to about 10. Exemplary of suitable tertiary amine bases for use in the present invention are trialkylamines such as trimethylamine, triethylamine, tri-n-propylamine, ethyldimethylamine, benzyldiethylamine and the like; dialkylarylamine such as dimethylaniline, diethylaniline, N,N-diethyl-4-methylaniline, N-methyl-N-ethylaniline, N,N-dimethyltoluidine and the like; cyclic and bicyclic tertiary amines such as pyridine, collidine quinoline, isoquinoline, 2,6-lutidine, 2,4-lutidine, triethylenediamine, 1,5-diazabicyclo[4.3.0]nonene-5 (DBN), 1,5-diazabicyclo[5.4.0]undecene-5 (DBU), and like; and polymeric tertiary amine bases such as the copolymer formed from divinylbenzene and and vinylpyridine described by Hallensleben and Wurm in *Angew. Chem. Intl. Ed. Engl.*, 15, 163 (1976). Pyridine is a most preferred tertiary amine base.

The amount of tertiary amine base employed in the present process is usually dependent on the amount of halogenating agent used. Typically from about 1.0 to about 1.2 equivalents and preferably about one equivalent of tertiary amine base is employed for each equivalent of halogenating agent.

The process of the present invention is usually carried out at a temperature of about 30° C. or below. Preferably the present process is conducted at a temperature of about 0° C. or below and more preferably at about −10° C. or below. Usually the process is not conducted at a temperature less than about −70° C. Most preferred is a temperature range of about −10° to about −70° C.

It should be noted that the imino halide forming process of the present invention can be conducted at temperatures above 30° and below −70°. The freezing point of the reaction medium and substrate solubility are possible limiting factors at low temperatures while stability of the thermodynamically unstable halogenating agent and the product imino halides is the main considerations in avoiding selection of higher reaction temperatures. Of course, if the halogenating agent has been stabilized in solution with a tertiary amine base as described hereinabove, the upper temperature range for the present process becomes a less critical variable; higher temperature could easily be employed without significant loss of the halogenating agent and without detriment to the halogenation process itself.

Solvents which may be employed in the present process are the same as those described hereinabove for the preparation of the triaryl phosphite-halogen kinetic complexes. Preferred solvents are aromatic hydrocarbons or halogenated hydrocarbons.

The cephalosporin and penicillin imino halide products of the present process can be isolated and purified by conventional laboratory techniques including, for example, extraction, crystallization and recrystallization, and trituration. Because these products are sensitive to acid catalyzed alcoholysis or hydrolysis and to nucleophilic attack, some precaution should be taken during product isolation to avoid exposing the products to conditions under which such reactions of the imino halide might take place. Since the primary utility of the imino halide products is as intermediates to the corresponding C-6 aminopenicillins or C-7 aminocephalosporins, preferably the imino halide products of the present process are reacted without isolation from the halogenating reaction mixture with an excess of a $C_1$-$C_{15}$ aliphatic alcohol or more preferably a β-disubstituted primary aliphatic alcohol or a 1,2- or 1,3-diol to provide the corresponding nucleus esters.

The improved alcoholysis of cephem imino halides via an imino ether intermediate using β-disubstituted aliphatic alcohols and 1,2- or 1,3-diols to provide cephem nucleus esters is disclosed in U.S. Pat. Nos. 3,845,043, issued Oct. 29, 1974, and 3,868,368 issued Feb. 25, 1975 respectively.

Preferred for imino etherification and subsequent alcoholysis of the present iminohalides are a $C_4$-$C_{12}$ β-disubstituted primary aliphatic alcohol, a $C_3$-$C_{15}$ aliphatic 1,3-diol, or a $C_2$-$C_{12}$ aliphatic 1,2-diol.

Suitable β-disubstituted primary aliphatic alcohols are those compounds of the formula

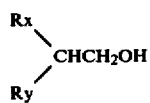

wherein each of Rx and Ry is an alkyl group such that the β-disubstituted primary aliphatic alcohol has from 4 to about 12 carbon atoms or Rx and Ry are taken together with the carbon atom to which they are bonded to form a cycloalkyl group having from 5 to 8 carbon atoms. Exemplary of such alcohols are isobutanol, 2-methylbutanol, 2-ethylbutanol, 2-ethylhexanol, hydroxymethylcyclopentane, hydroxymethylcyclohexane, 2-n-butyloctanol, 2-n-propylhexanol and like alcohols. Suitable 1,2 or 1,3-diols are those of the formula

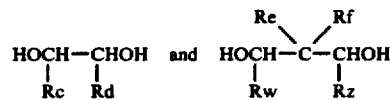

respectively wherein Rc and Rd are hydrogen or alkyl such that the 1,2-diol has from 2 to 12 carbon atoms and wherein Rw and Rz are each hydrogen, methyl or ethyl, and each of Re and Rf is hydrogen or a hydrocarbon moiety such that the 1,3-diol has from 3 to 15 carbon atoms. Representative of 1,2-diols are 1,2-propylene glycol, 2,3-butanediol, 1,2-butanediol, 3,4-pentanediol, and 3,4-hexanediol. Representative of 1,3-diols are 1,3-propanediol, 1,3-butanediol, 1,3-pentanediol, 2,2-dimethyl-1,3-propanediol, 2,2-diethyl-1,3-propanediol, 2,4-pentanediol, and 2,2-diphenyl-1,3-propanediol. Most preferred of alcohols or diols for cleavage of the imino-halide products of the present process are isobutanol, 1,2-propanediol and 1,3-propanediol.

An excess of the alcohol or diol is employed for cleavage of the imino halide products of the present invention. The amount of excess alcohol or diol is not critical. When the afore-described 1,2- or 1,3-diols are employed about a 2-3 fold excess will suffice. When a β-disubstituted primary aliphatic alcohol is employed about a 3-6 fold excess is usually preferred. Of course larger amounts of the alcohol or diol may be employed without affecting the course of the reaction. Often a 10-15 fold excess of the preferred alcohol or diol is used. When aliphatic alcohols other than those mentioned hereinabove as preferred are used to cleave the imino halide products of the present process, larger excesses, about 10-100 fold, are typically employed.

Usually the alcohol or diol is simply added to the halogenating reaction mixture in which the imino chloride has been prepared in accordance with the process of the present invention.

Alcoholysis of the imino chloride (via imino ether formation) is acid catalyzed. The reaction mixture itself is usually acidic enough so that alcoholysis occurs upon alcohol or diol addition without the addition of acid to the reaction mixture. However, to enhance the rate of alcoholysis and therefore the rate of nucleus ester formation, the reaction mixture is preferably acidified with, for example, hydrogen chloride after the alcohol or diol has been added to the reaction mixture. This can be accomplished simply by bubbling HCl gas into the reaction mixture for a short period of time. Typically at least about 1 equivalent of hydrogen chloride is added to the reaction mixture to promote nucleus ester formation.

The product nucleus esters can be isolated often as their crystalline hydrochloride salts simply by filtering the crystallized product from the reaction mixture. Non-crystalline nucleus esters produced in accordance with the present procedure can be isolated from the reaction mixture using conventional laboratory techniques. Alternatively the nucleus esters can be reacted (acylated) in solution, without being isolated. Acylation of the nucleus esters using well known laboratory procedures provides C-6 acylamino penicillin esters or C-7 acylamino cephalosporins esters which either can be deesterified to provide known antibiotic compounds or they can be used as intermediates for further chemical modification.

The following examples are provided to further illustrate the present invention. It is not intended that this invention be limited in scope by reason of any of these examples. In the following examples and preparations nuclear magnetic resonance spectra are abbreviated nmr. The nuclear magnetic resonance spectra were obtained on a Varian Associates T-60 Spectrometer using tetramethylsilane as the reference standard. The chemical shifts are expressed in δ values in parts per million (ppm) and coupling constants (J) are expressed as Hz (cycles per second).

EXAMPLE 1

4'-Nitrobenzyl 7-(1-chloro-2-phenylethylidene)imino-3-methyl-3-cephem-4-carboxylate.

Into 50 ml of methylene chloride at −15° C. was bubbled chlorine gas while simultaneously 3.2 ml (12.3 mmol) of triphenyl phosphite (TPP) was added dropwise to the solution. The chlorine and TPP were combined at such a rate that the faint yellow color of chlorine could be noted in the reaction mixture throughout the co-addition. Near the end of the TPP addition, chlorine addition was discontinued. TPP was then added until the yellow color of the reaction mixture was dissipated. Additional chlorine and the remaining TPP were then added to the reaction mixture until the last drop of TPP dissipated the chlorine color.

To the resulting solution of the prepared triphenyl phosphite-chlorine kinetic complex (TPP-C) at −15° C. was added 4.68 gm (10 mmol) of 4-nitrobenzyl 7-phenylacetamido-3-methyl-3-cephem-4-carboxylate and, dropwise over a period of 12 minutes, a solution of 1.01 ml (12.5 mmol) of pyridine in 4 ml of methylene chloride. The reaction mixture was stirred at −10° to −15° for another 15 minutes after which time was added 2.1 ml of propylene oxide. The cooling bath was removed and the reaction mixture was stirred an additional 15 minutes as the temperature rose to about 0° C. The reaction mixture was washed with 25 ml of water, dried over calcium chloride dihydrate and evaporated in vacuo to a syrup which subsequently crystallized. The product thereby obtained was pulverized under 25 ml of diethyl ether containing six drops of propylene oxide, filtered, washed with ether, and dried in a vacuum at room temperature to provide 4.58 gm (94.2%) of the title product as snow white crystals, m.p. 132°–133° C.

nmr (CDCl$_3$), pyridine d-5) δ 2.18 (s, 3), 3.37 (ABq, 2, J=16 Hz), 3.96 (s, 2), 5.05 (d, 1, J=5 Hz), 5.37 (s, 2), 5.5 (d, 1, J=5 Hz), 7.3 (s, 5, ArH), and 7.4–8.4 (m, 4, ArH). Anal calcd for C$_{23}$H$_{20}$N$_3$O$_5$SCl: C, 56.35; H, 4.15; N, 8.65; S, 6.60; Cl, 7.30. Found: C, 56.60; H, 4.25; N, 8.83; S, 6.49; Cl, 7.07.

EXAMPLE 2

2',2',2'-Trichloroethyl 6-(1-chloro-2-phenyl ethylidene)imino penicillanate.

A solution of approximately 12.3 mmol of the triphenyl phosphite-chlorine complex in 45 ml of methylene chloride was prepared in accordance with the procedure described in Example 1. To this solution at −30° C. was added 4.66 gm (10 mmol) of 2',2',2'-trichloroethyl 6-phenylacetamido penicillanate. An additional 5 ml of methylene chloride was used to wash the penicillin ester into the reaction mixture. To the resulting solution was added dropwise over a 20 minute period a solution of 1.01 ml (12.5 mmol) of pyridine in 4 ml of methylene chloride. The reaction mixture was stirred at −20° to −30° C. for about 15 minutes after which time 2.1 ml of propylene oxide was added to the mixture to destroy any HCl or excess chlorinating reagent remaining in the reaction mixture. After the reaction mixture was allowed to warm to approximately 0° C. over a 15 minute period, the solution was washed with 25 ml of ice water and dried over calcium chloride dihydrate. Evaporation in vacuo of the dried solution provided 11 gm of an oil which crystallized upon the addition of about 1 ml of diethyl ether. An additional 25 ml of diethyl ether containing 4 drops of propylene oxide was added to the crystallized product. After stirring at room temperature for 5 minutes, the white crystalline product was filtered, washed with 25 ml of diethyl ether and dried under reduced pressure at room temperature. The title product, 2.52 grams, was obtained: m.p. 84°–85.5° C. An addition crop of 1.06 gm of the title product was obtained by evaporating the filtrate in vacuo to 12 grams of a slurry which was diluted with 20 ml of a 1:1 ether, hexane solution. Total yield - 74%.

nmr (CCl$_4$) δ 1.56 (s, 3), 1.68 (s, 3), 3.96 (s, 2), 4.57 (s, 1), 4.8 (s, 2), 5.3 (d, 1, J=4 Hz), 3.93 (d, 1, J=4 Hz) and 7.3 (s, 5). Anal calcd for C$_{18}$H$_{18}$N$_2$O$_3$SCl$_4$: C, 44.65; H, 3.75; N, 5.78; S, 6.62; Cl, 29.29. Found: C, 44.76; H, 3.84; N, 5.90; S, 6.71; Cl, 29.06.

EXAMPLE 3

4'-Nitrobenzyl 7-(1-chloro-2-phenoxyethylidene)imino-3-chloro-3-cephem-4-carboxylate.

A solution of about 12.3 mmol of the triphenyl phosphite chlorine-complex in 45 ml of methylene chloride was prepared in accordance with the procedure described in Example 1. To this solution at −15° C. was added 5.04 gm (10 mmol) of 4'-nitrobenzoyl 7-phenoxyacetamido-3-chloro-3-cephem-4-carboxylate which was washed into the reaction mixture with an additional 5 ml of methylene chloride. Immediately a solution of 1.01 ml (12.5 mmol) of pyridine in 4 ml of methylene chloride was added dropwise over a 15 minute period to the reaction mixture. After the reaction mixture was stirred for an additional 15 minutes at −10° to −15° C., 2.1 ml of propylene oxide was added. The cooling bath was removed, and the temperature of the mixture was allowed to rise to about 0° over a 15 minute period after which time the rection mixture was washed with 25 ml of ice water, dried over calcium chloride dihydrate and subsequently evaporated in vacuo to about 20 grams of a syrup. No crystals were observed after the addition of about 50 ml of diethyl ether to the product residue. After the ether was decanted from the product residue, the product residue was further dried in vacuo to 11 grams of a thick oil. This product residue was washed three times with 50 ml portions of 1:1 ether, hexane. Trituration of the resulting thick oil with 25 ml of diethyl ether resulted in crystallization of the product. The crystallized product was filtered, washed with ether, and vacuum dried at room temperature to provide 3.58 grams (68.6%) of the title product as light colored crystals: m.p. 94°–97° C.

nmr (CDCl$_3$, pyridine d-5) δ 3.56 (ABq, 2, J=18 Hz), 4.8 (s, 2), 5.13 (d, 1, J=5 Hz), 5.3 (s, 2), 5.53 (bd, 1, J=5 Hz) and 6.8–8.3 (m, 9). Anal calcd for C$_{22}$H$_{17}$N$_3$O$_6$SCl$_2$: C, 50.59; H, 3.28; N, 8.04; S, 6.14; Cl, 13.57. Found: C, 50.32; H, 3.36; N, 8.20; S, 5.92; Cl, 13.57.

EXAMPLE 4

4'-Nitrobenzyl 6-(1-chloro-2-phenoxyethylidene)imino penicillanate.

A solution of 9.71 gm (20 mmol) of 4'-nitrobenzyl 6-phenoxyacetamido penicillanate in 75 ml of methylene chloride was dried over calcium chloride dihydrate for about 15 minutes. The solution was filtered and evaporated to about 40 ml for addition of the TPP-C preparation. A solution of about 24.3 mmol of the triphenyl phosphite chlorine complex in about 50 ml of methylene chloride was prepared at −15° to −20° C. in accordance with the procedures described in Example 1. The solution of TPP-C was cooled to −40° C. and the above-prepared solution of the penicillin ester was added. The temperature of the reaction mixture rose to about −22° C. A solution of 2.02 ml (25 mmol) of pyridine in 8 ml of methylene chloride was then added dropwise over a 15 minute period to the reaction mixture at −20° to −30° C. After stirring the mixture for about 15 minutes 4.2 ml of propylene oxide (60 mmol) was added. After the reaction mixture was allowed to warm to 0° C. over about a 15 minute period, it was washed quickly with 50 ml of ice water and dried over calcium chloride dihydrate. The dried solution was filtered and evaporated under-reduced pressure to about 27 grams of solution. Successively, a 50 ml volume of ether and two 20-ml volumes of carbon tetrachloride were added; the resulting solution was each time subsequently evaporated in vacuo to a product oil. The nuclear magnetic resonances spectrum of this crude product showed it to be the title product contaminated with triphenyl phosphate.

nmr (CDCl$_3$) δ 1.33 (s, 3), 1.46 (s, 3), 4.46 (s, 1), 4.8 (s, 2), 5.2 (s, 2), 5.3 (d, 1, J=4 Hz), 5.57 (d, 1, J=4 Hz), and 6.7–8.3 (m, 9).

EXAMPLE 5

4'-Nitrobenzyl 7-(1-chloro-1-phenoxyethylidene)imino-3-acetoxy-3-cephem-4-carboxylate.

Chlorine gas was bubbled into 45 ml of methylene chloride cooled to −10° C. simultaneously with the dropwise addition of 3.16 ml (12 mmol) of triphenyl phosphite. The co-addition of these reactants were monitored so as to maintain a slight yellow color (excess of chlorine) throughout the preparation until the last drop of phosphite added dissipated the yellow color. To the resulting solution was added 5.28 gm (10 mmol) of 4'-nitrobenzyl 7-phenoxyacetamido-3-acetoxy-3-cephem-4-carboxylate which was washed into the reaction mixture with 5 ml of methylene chloride. Thereafter 1.01 ml (12.5 mmol) of pyridine in 5 ml of methylene chloride was added dropwise over a 15 minute period to the reaction mixture at −10° C. After stirring the mixture for an additional 15 minutes at −10° C., 2.1 ml (30 mmol) of propylene oxide was added. After stirring for 10 minutes at 0° C. the mixture was washed with 50 ml of ice water, dried over calcium chloride, and evaporated in vacuo to an oil. Attempts to crystallize the product from ether failed. After evaporating at reduced pressure all solvents from the product residue, 25 ml of carbon tetrachloride was added and the resulting solution again evaporated to dryness. An nmr spectrum of the unpurified product showed it to be the title iminochloride.

nmr (CDCl$_3$) δ 2.06 (s, 3), 3.41 (ABq, 2, J=18 Hz), 4.83 (s, 2), 5.05 (d, 1, J=5 Hz), 5.28 (s, 2), 5.56 (bd, 1, J=5 Hz) and 6.8–8.3 (m, ArH).

EXAMPLE 6

4'-Nitrobenzyl 7-[1-chloro-2-(2-thienyl)ethylidene]imino-3-methyl-3-cephem-4-carboxylate.

Following the procedure described in Example 1 a solution of about 12 mmol of the triphenyl phosphite chlorine-complex in 45 ml of methylene chloride was prepared. To that solution at −10° C. was added 4.74 gm (10 mmol) of 4'-nitrobenzyl 7-(2-thienylacetamido)-3-methyl-3-cephem-4-carboxylate which was washed into the reaction mixture with an additional 5 ml of methylene chloride. After 5 minutes 1.01 ml (12.5 mmol) of pyridine in 5 ml of methylene chloride were added dropwise over a 20 to 30 minute period. The reaction mixture was stirred at −10° C. for about 30 minutes after which time the reaction mixture was allowed to warm to room temperature and to stir for approximately 2 hours. To the reaction mixture was then added 2.1 ml (30 mmol) of propylene oxide. After 10 minutes the mixture was washed with 50 ml of ice water, dried over calcium chloride dihydrate, and evaporated under reduced pressure to an oil. The product oil was crystallized by adding a 1:1 mixture of methylene chloride and ether. Filtration of the crystallizing mixture provided 2.03 grams (41.3%) of the title product: m.p. 129°–132° C. An additional 1.95 grams (39.6%) of the title product was obtained by evaporation of the filtrate from the crystallizing mixture. Total yield - 80.9%.

nmr (CDCl$_3$) δ 2.16 (s, 3), 3.33 (ABq, 2, J=18 Hz), 4.16 (s, 2), 5.03 (d, 1, J=4 Hz), 5.33 (s, 2), 5.5 (bd, 1, J=4 Hz), and 6.8–8.4 (m, ArH). Anal calcd for C$_{21}$H$_{18}$N$_3$O$_5$S$_2$Cl: C, 51.27; H, 3.69; N, 8.54; S, 13.03. Found: C, 51.30; H, 3.72; N, 8.31; S, 12.91.

EXAMPLE 7

4'-Nitrobenzyl 7-(α-chlorobenzylidene)imino-3-methyl-3-cephem-4-carboxylate.

A solution of the triphenyl phosphite chlorine complex was prepared in 45 ml of methylene chloride using 3.16 ml (12 mmol) of triphenyl phosphite in accordance with the procedures described in Example 1 above. To this solution at −10° C. were added 4.14 gm (10 mmol) of 4'-nitrobenzyl 7-benzamido-3-methyl-3-cephem-4-carboxylate and 1.01 ml (12.5 mmol) of pyridine. The reaction mixture was removed from the ice bath and immediately exothermed to 0° C. After stirring the reaction mixture for about 3 minutes the iminochloride began to crystallize. After one hour at room temperature the reaction mixture was filtered to provide a crystalline product which was washed with ether and dried. 2.28 gm (48.3%) of the title product was isolated: m.p. 175° C.

The filtrate from above was diluted with methylene chloride and washed successively with dilute HCl and sodium chloride solutions and subsequently dried over calcium chloride dihydrate. Evaporation in vacuo of the resulting dried solution gave an oil which, upon trituration with diethyl ether, provided a second crop of crystals of the title product which were filtered, washed with ether and dried. 1.72 gm (36.4%) of the title product was isolated from the filtrate. Total yield - 84.7%.

nmr (CDCl$_3$) δ 2.20 (s, 3), 3.43 (ABq, 2, J=18 Hz), 5.15 (d, 1, J=5 Hz), 5.37 (s, 2), 5.75 (d, 1, J=5 Hz) and 7.2–8.4 (m, ArH). Anal calcd for $C_{22}H_{18}N_3O_5SCl$: C, 55.99; H, 3.84; N, 8.90; S, 6.79; Cl, 7.51. Found: C, 56.16; H, 4.06; N, 9.00; S, 6.54; Cl, 7.67.

EXAMPLE 8

4'-Nitrobenzyl 7-(1-chloro-2-phenoxyethylidene)imino-3-methyl-3-cephem-4-carboxylate.

A solution of the triphenyl phosphite-chlorine complex was prepared in 45 ml of methylene chloride from 3.95 ml (15 mmol) of triphenyl phosphite and chlorine in accordance with the procedures described in Example 1. To this solution was added 4.84 gm (10 mmol) of 4'-nitrobenzyl 7-phenoxyacetamino-3-methyl-3-cephem-4-carboxylate which was washed into the reaction mixture with 5 ml of methylene chloride. Then 1.3 ml (15.6 mmol) of pyridine in 8 ml of methylene chloride was added dropwise over a 30 minute period to the reaction mixture at −10° C. The reaction mixture was then removed from the ice bath and allowed to stir for 30 minutes after which time 2.1 ml (30 mmol) of propylene oxide was added. After 10 minutes the reaction mixture was washed with 50 ml of ice water, dried over calcium chloride dihydrate, and evaporated in vacuo to an oil which crystallized with the addition of 50 ml of diethyl ether. Filtration provided 3.44 grams (68.6%) of the title product: m.p. 110°–111° C.

nmr (CDCl$_3$, pyridine d-5) δ 2.16 (s, 3), 3.26 (ABq, 2, J=18 Hz), 4.83 (s, 2), 5.01 (d, 1, J=5 Hz), 5.28 (s, 2), 5.52 (bd, 1, J=5 Hz) and 6.7–8.2 (m, ArH).

EXAMPLE 9

4'-Nitrobenzyl 7-(1-chloro-2-phenoxyethylidene)imino-3-methylenecepham-4-carboxylate/4'-nitrobenzyl 7-amino-3-methylenecepham-4-carboxylate hydrochloride.

A solution of about 12.3 mmol of triphenyl phosphitechlorine compound was prepared in accordance with the procedures described in Example 1. To that solution were added 4.84 gm (10 mmol) of 4'-nitrobenzyl 7-phenoxyacetamido-3-methylenecepham4-carboxylate and a solution of 1.01 ml (12.5 mmol) of pyridine in 4 ml of methylene chloride dropwise over a 15 minutes period. The reaction was stirred for about 15 minutes at −10° to −15° C. before adding 2.1 ml (30 mmol) of propylene oxide. After 15 minutes the reaction was washed quickly with 25 ml of ice water, dried over calcium chloride dihydrate for about 5 minutes, and evaporated in vacuo to provide about 11 grams of a thick oil which was dissolved in 25 ml of carbon tetrachloride. An nmr spectrum of the product obtained by evaporating the carbon tetrachloride solution showed the product to be the title iminochloride contaminated only with triphenyl phosphate.

nmr (CCl$_4$) δ 3.4 (ABq, 2), 4.87 (s, 2), 5.30 (m, 3), 5.45 (s, 2) and 6.7–8.4 (m, ArH).

The unpurified iminochloride was dissolved in 50 ml of methylene chloride and treated with 5.1 ml (55 mmol) of isobutanol and HCl gas. The temperature of the reaction mixture rose from about 20° to about 30° C. before a cooling bath was applied to the crystallizing mixture. After two hours at room temperature the product was filtered, washed, and dried to provide 3.58 grams (92.7%) of near white crystals of 4'-nitrobenzyl 7-amino-3-methylenecepham-4-carboxylate hydrochloride: m.p. 180°–181° C.

nmr (DMSO d-6) δ 3.67 (bs, 2), 5.0 (d, 1, J=5 Hz), 5.35–5.53 (m, 6), and 7.6–8.4 (m, ArH).

EXAMPLE 10

4'-Nitrobenzyl 7-amino-3-methyl-3-cephem-4-carboxylate hydrochloride.

To a solution of 4.1 ml of isobutanol (44 mmol) in 40 ml of methylene chloride at 25° C. was added 2.89 gm (8 mmol) of 4'-nitrobenzyl 7-(1-chloro-2-phenylethylidene)imino-3-methyl-3-cephem-4-carboxylate prepared in Example 1. The resulting solution was treated with HCl gas at a moderate rate for about 1 minute and 15 seconds. The title nucleus ester hydrochloride began precipitating as a gelatinous solid which soon crystallized and filled the solution as a paste. Because stirring was inefficient the reaction mixture was diluted with an additional 40 ml of methylene chloride. The resulting diluted alcoholysis mixture was stirred at room temperature for 2 hours and thereafter filtered to provide 2.52 grams (81.6%) of the title product: m.p. 183.5° C. The filtrate when treated with HCl gas yielded an additional 0.47 grams of the title product (m.p. 183.5° C.). Combined yield for the alcoholysis - 96.8%.

nmr (DMSO d-6) δ 2.21 (s, 3), 3.65 (ABq, 2, J=16 Hz), 5.18 (q, 2, J=4 Hz, β-lactam H), 5.41 (s, 2), and 7.6–8.4 (m, ArH).

EXAMPLE 11

4'-Nitrobenzyl 7-amino-3-methyl-3-cephem-4-carboxylate hydrochloride.

(A) From 4'-Nitrobenzyl 7-phenoxyacetamido-3-methyl-3-cephem-4-carboxylate.

A solution of the triphenyl phosphitechlorine complex was prepared by bubbling chlorine through a solution of 2.89 ml (11 mmol) of triphenyl phosphite in 50 ml of methylene chloride at −15° C. To this solution were added 5.02 gm (10 mmol) of 4'-nitrobenzyl 7-phenoxyacetamido-3-methyl-3-cephem-4-carboxylate and 0.85 ml (11.5 mmol) of pyridine. The reaction mixture was stirred for 1 hour at −15° to −10° C. after which time was added 6.0 ml (64.8 mmol) of isobutanol. The cooling bath was removed, and the reaction mixture was allowed to warm to room temperature over a 2 hour period. The titled nucleus hydrochloride ester, which began to crystallize in about 15 minutes, was filtered, washed with methylene chloride, and dried. A total of 3.55 grams (92%) of the title product was obtained as white crystals: m.p. 189° C. (decomp.).

(B) From 4'-Nitrobenzyl 7-heptanoylamido-3-methyl-3-cephem-4-carboxylate.

The experimental procedure described in Paragraph A above was repeated in detail using 4.61 gm (10 mmol) of 4'-nitrobenzoyl 7-heptanoylamido-3-methyl-3-cephem-4-carboxylate as the substrate. A total of 6.32 grams (93.8%) of the nucleus ester hydrochloride as snow white crystals was isolated: m.p. 188.5° C. (decomp.).

(C) From 4'-Nitrobenzyl 7-phenoxyacetamido-3-methyl-3-cephem-4-carboxylate in tetrahydrofuran.

A solution of the triphenyl phosphite-chlorine complex was prepared by bubbling chlorine into a solution of 11 mmol of triphenyl phosphite in tetrahydrofuran (THF) at −10° C. To the solution was added 4.84 gm (10 mmol) of 4'-nitrobenzyl 7-phenoxyacetamido-3-methyl-3-cephem-4-carboxylate. Subsequently 0.95 ml (11 mmol) of pyridine were added to the reaction mixture. The reaction was then allowed to stir at −10° C. for 1 hour after which time it was allowed to warm to room temperature and stir for another 2 hours. Then 6.0 ml (65 mmol) of isobutanol was added. After 2 hours the reaction mixture was filtered. The crystalline nucleus hydrochloride ester thereby obtained was washed with THF and dried. Total yield - 3.03 grams (78.5%): m.p. 151°–153° C. (dec.).

(D) From 4'-Nitrobenzyl 7-phenoxyacetamido-3-methyl-3-cephem-4-carboxylate in acetonitrile.

A solution of triphenyl phosphite-chlorine complex was prepared by bubbling chlorine into a solution of about 11 mmol of triphenyl phosphite in 45 ml of acetonitrile at −10° C. To this solution were added 4.84 gm (10 mmol) of 4'-nitrobenzyl 7-phenoxyacetamido-3-methyl-3-cephem-4-carboxylate and subsequently 0.95 ml (11 mmol) of pyridine at −10° C. After the reaction mixture was allowed to stir for 2 hours at −10° C. The ice bath was removed. After an additional 2 hours, 6.0 ml (65 mmol) of isobutanol was added to the reaction mixture. With seeding the product crystallized, and after stirring for 1 hour, it was filtered, washed with acetonitrile, and dried. Total yield - 2.55 grams (66.1%): m.p. 184° C. (dec.).

(E) From 4'-Nitrobenzyl 7-phenoxyacetamido-3-methyl-3-cephem-4-carboxylate in ethyl acetate.

The same procedure was followed as described in Paragraph D above except that ethyl acetate was used as a solvent for the triphenyl phosphite-chlorine reagent formation and for the cleavage process. Total yield 2.48 grams (64.2%): m.p. 177°–179° C. (dec.).

(F) From 4'-Nitrobenzyl 7-phenoxyacetamido-3-methyl-3-cephem-4-carboxylate using tri-o-tolyl phosphite-chlorine complex.

A solution of tri-o-tolyl phosphitechlorine complex was prepared as follows: 3.91 gm (11 mmol) of tri-o-tolyl phosphite was added to 45 ml of methylene chloride and cooled to −10° C. under a nitrogen atmosphere. Chlorine gas was bubbled into the solution until the yellow color persisted. Then about 0.5 mmol of tri-o-tolyl phosphite was added to discharge the yellow color. To the solution were added 4.84 gm (10 mmol) of 4'-nitrobenzyl 7-phenoxyacetamido-3-methyl-3-cephem-4-carboxylate and 1.01 ml (12.5 mmol) of pyridine. The reaction mixture was removed from the cooling bath and stirred for 90 minutes after which time 5.1 ml (55 mmol) of isobutanol was added. The product began to crystallize about 5 minutes after gaseous HCl was bubbled into the reaction mixture. After 90 minutes the reaction mixture was filtered. The product was washed with 25 ml of methylene chloride and dried at reduced pressure. Total yield—3.46 grams (89.6%): m.p. 184° C. (dec.).

(G) From 4'-Nitrobenzyl 7-phenoxyacetamido-3-methyl-3-cephem-4-carboxylate using divinylbenzene-vinylpyridine copolymer as the base.

A solution of the triphenyl phosphite-chlorine kinetic complex was prepared in 50 ml of methylene chloride at −10° C. by first bubbling chlorine through the solution and then adding dropwise triphenyl phosphite at such a rate that the yellow of the chlorine always persisted. When the dropwise addition of the triphenyl phosphite was about complete, the addition of chlorine was discontinued. Triphenyl phosphite was then added until the solution decolorized. A total of 3.0 ml (11.4 mmol) of triphenyl phosphite was used. To this solution was added 5.0 gm (10.3 mmol) of 4'-nitrobenzyl 7-phenoxyacetamido-3-methyl-3-cephem4-carboxylate followed immediately by 5.0 gm of divinylbenzene-vinylpyridine copolymer. The reaction mixture was removed from the cooling bath and stirred for 2 hours at room temperature. The polymer was then filtered and washed with about 20 ml of methylene chloride. The filtrate was treated with 6.0 ml (64.8 mmol) of isobutanol. HCl gas was then bubbled through the mixture for about 2 minutes. The nucleus hydrochloride product began to crystallize in about 3 minutes, and after one hour, was filtered from the mixture, washed with methylene chloride and dried. A total of 2.98 grams (75%) of the nucleus hydrochloride ester was isolated: m.p. 183° C. (dec.).

(H) From 4'-Nitrobenzyl 7-phenoxyacetamido-3-methyl-3-cephem-4-carboxylate using tri(p-methoxyphenyl)phosphite-chlorine complex.

A solution of tri(p-methoxyphenyl)phosphite chlorine complex was prepared as follows: 4.6 mg (11.5 mmol) of tri(p-methoxyphenyl)phosphite in about 5 ml of methylene chloride was added dropwise to 45 ml of methylene chloride at −10 to −20° C. with simultaneous addition of chlorine to a colorless endpoint. After the addition of all of the phosphite reagent, additional chlorine was added to give a faint yellow color; the color of excess chlorine rapidly dissipated without adding more phosphite. To the resulting solution was added 4.84 gm (10 mmol) of 4'-nitrobenzyl 7-phenoxyacetamido-3-methyl-3-cephem-4-carboxylate which was washed into the reaction mixture with 5 ml of methylene chloride. Subsequently a solution of 1.01 ml of pyridine (12.5 mmol) in 4 ml of methylene chloride was added dropwise to the reaction mixture over a 15 minute period. After stirring the reaction mixture for 15 minutes at −10°, 5.1 ml of isobutanol (55 mmol) was added to the reaction mixture. HCl gas was bubbled into the reaction mixture, and shortly thereafter the cooling bath was removed. After 2 hours at room temperature the reaction mixture was filtered to provide 0.89 grams (23%) of the nucleus hydrochloride ester: m.p. 173°–174° C.

(I) From 4'-Nitrobenzyl 7-phenoxyacetamido-3-methyl-3-cephem-4-carboxylate using triethylamine as the base.

A solution of the triphenyl phosphite-chlorine kinetic complex was prepared by adding chlorine gas simultaneously with 3.16 ml (12 mmol) of triphenyl phosphite to 45 ml of methylene chloride at −10° C. A slight yellow color was maintained throughout the preparation. An additional 0.5 mmol of triphenyl phosphite was added to dissipate the yellow chlorine color. To the resulting solution was added 4.84 gm (10 mmol) of 4'-nitrobenzyl 7-phenoxyacetamido-3-methyl-3-cephem-4-carboxylate which was washed into the mixture with 5 ml of methylene chloride. After 5 minutes 1.8 ml (13 mmol) of triethylamine in 8 ml of methylene chloride were added over a 15 minute period. After stirring the reaction mixture for 15 minutes at −10° C., the cooling bath was removed from the reaction mixture and 5.1 ml (55 mmol) of isobutanol was added. Thereafter HCl gas was bubbled into the reaction mixture for about 3 minutes. The reaction mixture was seeded and allowed to warm to room temperature. After 2 hours at room temperature the reaction mixture was filtered to provide 1.28 grams (33.2%) of the nucleus hydrochloride ester: m.p. 180.5° C. (dec.).

(J) From 4'-Nitrobenzyl 7-phenoxyacetamido-3-methyl-3-cephem-4-carboxylate using DBU as the base.

The same experimental procedure was followed as described in Paragraph I above except that 1.95 ml (13 mmol) of 1,5-diazabicyclo[5.4.0]undec5-ene (DBU) was used in place of the triethylamine base. 0.59 gm (15.3%) of nucleus ester hydrochloride product was isolated: m.p. 181° C. (dec.).

(K) From 4'-Nitrobenzyl 6-phenoxyacetamido penicillanate, 1-oxide.

A solution of 5.02 gm (10 mmol) of 4'-nitrobenzyl 6-phenoxyacetamido penicillanate, 1-oxide and 0.25 gm (1 mmol) of pyridinium di-chloromethanephosphonate in 88 ml of 1,1,2-trichloroethane was heated to reflux for 4 hours. The reaction mixture was evaporated in vacuo to a volume of about 44 ml.

A solution of 12 mmol of the triphenyl phosphite chlorine reagent was prepared by bubbling chlorine gas into a solution of 3.15 ml of triphenyl phosphite in 44 ml of 1,1,2-trichloroethane at −10° C. The chlorine gas was bubbled into the solution until a yellow color persisted. The yellow color was then discharged by the addition of a drop of triphenyl phosphite.

The solution from the first paragraph above was then added to the solution (at −10° C.) of the triphenyl phosphite-chlorine reagent. Thereafter 0.89 ml (11 mmol) of pyridine was added to the reaction mixture at −10° C. After 30 minutes at that temperature the reaction mixture was removed from the ice bath and allowed to warm to room temperature. After 30 minutes an additional 0.42 ml (5 mmol) of pyridine was added. After stirring the reaction mixture for an additional 30 minutes, 9.25 ml (100 mmol) of isobutanol was added. The product crystallized as the reaction mixture was stirred overnight. Filtration provided 2.67 grams (69.2%) of the nucleus ester hydrochloride: m.p. 183° C. (dec.).

(L) From 4'-Nitrobenzyl 6-phenoxyacetamido penicillanate, 1-oxide using 2,6-lutidiene as the base.

The same experimental procedure was followed as described in Paragraph K above except that 1.25 ml (11 mmol) of 2,6-lutidine was used in place of pyridine. Also HCl gas was bubbled into the reaction mixture for about 60 seconds after the addition of isobutanol. The product began to crystallize in about 2 to 3 minutes after the HCl addition. A total of 2.47 gm (64%) of the nucleus ester hydrochloride was isolated: m.p. 173° C. (dec.).

EXAMPLE 12

4'-Nitrobenzyl 7-amino-3-methoxy-3-cephem-4-carboxylate, hydrochloride.

Chlorine was bubbled through a stirred solution of 0.4 ml (1.5 mmol) of triphenyl phosphite in 10 ml of methylene chloride at −10° C. until the light yellow green color of excess chlorine persisted. One small drop of triphenyl phosphite discharged the color completely. To the resulting solution was added 0.5 gm (1 mmol) of 4'-nitrobenzyl7-phenoxyacetamido-3-methoxy-3-cephem-4-carboxylate followed by 0.12 ml (1.5 mmol) of pyridine. The reaction mixture was removed from the cooling bath and stirred 1.5 hours at room temperature after which time 0.6 ml (6.4 mmol) of isobutanol was added. The title nucleus hydrochloride begin to crystallize from the reaction mixture within 5 minutes after the addtion of the alcohol. After 1.5 hours the reaction mixture was filtered to provide 0.3 gm (75%) of the title product as off-white crystals: m.p. 185° C. (dec.).

nmr (DMSO d-6) δ3.92 (bs, 2), 4.0 (s, 3), 5.02 (d, 1, J=5 Hz), 5.32 (d, 1, J=5 Hz), 5.45 (s, 2) and 7.6–8.4 (m, ArH). Anal calcd for $C_{15}H_{16}N_3O_6SCl$: C, 44.84; H, 4.01; N, 10.46; Cl, 8.82; S, 7.98. Found: C, 44.69; H, 4.17; N, 10.34; Cl, 9.05; S, 7.77.

EXAMPLE 13

4'-Nitrobenzyl 7-amino-3-methylenecepham-4-carboxylate, hydrochloride

To a solution of 5.02 gm (10 mmol) of 4'-nitrobenzyl 7-phenoxyacetamido-3-methylenecepham-4-carboxylate, 1-oxide and 2.4 ml (22.5 mmol) of amylene in 50 ml of methylene chloride at 15° C. was added dropwise over 10 minutes 1.67 ml (22.5 mmol) of acetyl bromide. The reaction mixture was cooled to 0° C., 25 ml of ice water were added, and the reaction mixture was then allowed to stir for 30 minutes. The methylene chloride layer was separated, washed successively with 25 ml of water and 25 ml of dilute sodium chloride solution, dried over anhydrous sodium sulfate and evaporated in vacuo to a volume of 25 ml.

A solution of the triphenyl phosphitechlorine kinetic complex was prepared by bubbling chlorine gas into a solution of 2.89 ml (11 mmol) of triphenyl phosphite in 25 ml of methylene chloride at −10° C. until the yellow color persisted. Another 0.12 ml (0.46 mmol) of triphenyl phosphite was added to the solution to discharge the yellow color. To the resulting solution at −10° C. was added a solution prepared in the foregoing paragraph. Then 0.93 ml (11.5 mmol) of pyridine was added. The reaction mixture was then removed from the ice bath and allowed to warm to room temperature. After 1 hour, 5.1 ml (55 mmol) of isobutanol was added to the reaction mixture. The product began to crystallize in the reaction mixture after about 10 minutes. After stirring the reaction mixture 90 minutes at room temperature, it was filtered to provide 3.17 gm (82.1%) of the title nucleus ester hydrochloride: m.p. 182° C. (dec.).

nmr (DMSO d-6) δ3.6 (bs, 2), 4.95 (d, 2, J=5 Hz), 5.33–5.7 (m, 6), and 7.6–8.4 (m, ArH).

EXAMPLE 14

Benzhydryl 7-amino-3-acetoxymethyl-3-cephem-4-carboxylate.

To a solution of 1.39 gm (1.5 mmol) of 2,4-dichlorobenzoyl cephalosporin C dibenzhydryl ester in 10 ml of methylene chloride at −35° C. was added 0.484 ml of pyridine (6 mmol). To the resulting solution was added a solution of the triphenyl phosphite-chlorine reagent prepared at −10° C. from 1.57 ml (6 mmol) of triphenyl phosphite and chlorine in 10 ml of methylene chloride. After 150 minutes at about 18° C. the reaction mixture was cooled to −5° C. and treated with 3.0 ml of isobutanol. The reaction mixture was allowed to warm to a temperature of about 20° C., after which time the solvent was evaporated from the reaction mixture leaving a dark brown syrup. The resulting product residue was dissolved in 20 ml of methylene chloride and 10 ml of water. The pH of the aqueous layer was adjusted to 0.9 with HCl. The methylene chloride layer was then separated and extracted with water at pH 7.5. The methylene chloride layer was then dried over magnesium sulfate and evaporated in vacuo to about 3.5 gm of a very dark brown syrup which was dissolved in 3.5 ml of a 3:7 ethyl acetate-toluene solution and applied to the surface of 40 grams of silica gel in a 9 mm column. Chromatography using at first a 3:7 ethyl acetate/toluene eluant mixture and then a 1:1 toluene:ethyl acetate eluant mixture provided a total 0.24 gm (36%) of the title product.

EXAMPLE 15

7-Amino-3-acetoxymethyl-3-cephem-4-carboxylic acid (7-ACA).

To a slurry of 2.94 gm (5 mmol) of 2,4-dichlorobenzoyl cephalosporin C, 0.16 ml (1.34 mmol) of quinoline, and 2.39 ml (15 mmol) of N,N-diethylaniline in 30 ml of methylene chloride at room temperature were added 2.45 ml (34.5 mmol) of acetyl chloride. After the reaction mixture was cooled to $-25°$ C., 0.6 ml (3.75 mmol) of diethyl aniline, and a solution of the triphenyl phosphite-chlorine reagent derived from 3.68 ml (14 mmol) of triphenyl phosphite in 15 ml methylene chloride were added. The reaction mixture was then removed from the cooling bath and allowed to warm to room temperature over a 2 hour period. After the mixture was cooled to $-15°$ C., 8.5 ml. (116 mmol) of propylene glycol was added. The reaction mixture was stirred for approximately ½ hour at 20° C. after which time it was cooled to $-15°$ C. and then combined with 25 ml of ice water. The aqueous layer was separated, and its pH was adjusted to 3.5 with 3.3 ml of ammonium hydroxide. After stirring for 1½ hours in an ice bath the aqueous solution was filtered to provide 0.4 gm (29%) of 7-ACA.

EXAMPLE 16

7-Amino-3-methyl-3-cephem-4-carboxylic acid (7-ADCA).

To a slurry of 3.40 gm (10 mmol) of 7-phenoxyacetamido-3-methyl-3-cephem-4-carboxylic acid, 0.158 ml (1.34 mmol) of quinoline, and 2.38 ml (15 mmol) of N,N-diethylaniline in 30 ml. of methylene chloride at room temperature was added 2.46 ml (34.5 mmol) of acetyl chloride. The reaction mixture was allowed to stir for about 6 hours at a temperature of 18° to 22° C. The reaction mixture was then cooled to $-15°$ C. Then 0.6 ml (3.75 mmol) of N,N-diethylaniline and a solution of the triphenyl phosphitechlorine reagent derived from 3.68 ml of triphenyl phosphite and chlorine in 15 ml of methylene chloride, were added. The reaction mixture was then removed from the cooling bath and allowed to warm to near room temperature over the next seven minutes. The reaction mixture was then cooled to $-20°$ C. Then 10.7 ml (116 mmol) of isobutanol added. Again the reaction mixture was removed from the cooling bath. About 45 minutes after the addition of the alcohol, a copious amount of solid precipitate was observed. After an additional ½ hour at room temperature the reaction mixture was cooled to 0° C. and filtered to provide 1.95 gm (73%) of 7-ADCA. Some impurities were visible in an nmr spectrum of the product.

EXAMPLE 17

7-Amino-3-acetoxmethyl-3-cephem-4-carboxylic acid (7-ACA).

To a slurry of 4.18 gm (9.76 mmol) of 7-phenoxyacetamido-3-acetoxymethyl-3-cephem-4-carboxylic acid sodium salt, 0.154 ml (1.31 mmol) of quinoline and 2.91 ml (18.2 mmol) N,N-diethylaniline in 29 ml of methylene chloride at room temperature was added 2.40 ml (33.6 mmol) of acetyl chloride. After 1 hour and 15 minutes at room temperature the reaction mixture was cooled to $-35°$ C. To this mixture was added a solution of the triphenyl phosphite-chlorine kinetic complex prepared from 3.6 ml (13 mmol) of triphenyl phosphite and chlorine in 15 ml of methylene chloride. The reaction mixture was stirred at $-25°$ to $-20°$ C. for about 60 minutes after which time was added 10.5 ml of isobutanol. The mixture was allowed to warm to 0° at which temperature it was stirred for 2 hours. The reaction was then added to a mixture of 50 gm of ice and water. The aqueous layer was separated and its pH was adjusted to 3.5. The aqueous solution was then stirred for 1 hour in an ice bath under a stream of nitrogen. Filtration of the aqueous solution provided 2.7 grams (78%) of 7-ACA.

EXAMPLE 18

7-Amino-3-acetoxymethyl-3-cephem-4-carboxylic acid (7-ACA)

4.55 gm of cephalosporin C sodium salt was suspended in 142 ml of amylene inhibited chloroform. The solution was distilled to a volume of 67 ml. The chloroform suspension of cephalosporin C sodium salt was then cooled to 26° C. To that solution were added 0.464 ml (3.94 mmol) of quinoline, 6.95 ml (43.5 mmol) of diethylaniline, and 9.30 ml (131 mmol) of acetyl chloride. The mixture was then warmed with stirring to about 35° C. over a 7 minute period, after which time the heat source was removed. After stirring for 2 hours the reaction mixture was filtered using hyflo on paper over glass paper in a Buchner funnel.

A solution of the triphenyl phosphite-chlorine reagent prepared at $-20°$ C. by adding chlorine and triphenyl phosphite (8.9 ml, 34 mmol) simultaneously to 35 ml of chloroform, was added to a mixture of the filtrate from above at $-30°$ C. and 3.2 ml (20 mmol) of diethylaniline. The reaction mixture was stirred at $-20°$ to $-15°$ for 60 minutes after which time it was cooled to $-35°$ C. Propylene glycol (15 ml) was then added. After stirring the reaction mixture for 2 hours at 0° C., it was poured onto 51 gm of ice. The chloroform layer was separated and extracted again with another 5 gm of ice water. The aqueous extracts were combined, and the pH was adjusted to 3.5 with approximately 7.5 ml of ammonium hydroxide. The aqueous solution was then stirred for 60 minutes in an ice bath with an air stream blown over the surface to remove residual chloroform. The slurry was then filtered and the product washed successively with 6 ml of water, 15 ml of methanol and 5 ml of acetone. Total yield of the product 7-ACA (air dried) was 1.87 gm (73%).

EXAMPLE 19

7-Amino-3-acetoxymethyl-3-cephem-4-carboxylic acid (7-ACA)

(A) 4.8 gm (10 mmol) of cephalosporin C, sodium salt, dihydrate was suspended in 80 ml of methylene chloride (cyclohexane stabilized, dried over 4A molecular sieves). Diethyl aniline (dried over KOH), 7.4 gm (8 ml, 50 mmol), and acetyl chloride, 4.7 gm (4.3 ml, 60 mmol), were added. The mixture was stirred in an ice bath at 30° to 40° C. for 1 hour and then at room temperature for 2 hours. Filtration removed 1.65 gm of undissolved material. The reaction solution was cooled in an ice-alcohol bath before addition to a solution of the triphenyl phosphite-chlorine kinetic compound prepared as follows: triphenyl phosphite, 6.8 gm (5.8 ml, 22 mmol), was added to 100 ml of dry methylene chloride and cooled to ice-alcohol temperature before the addition of chlorine gas until a yellow coloration persisted. The addition of a few drops of triphenyl phosphite gave a colorless solution. After mixing the two above described solutions at ice alcohol temperature, diethyl aniline, 3.3 gm (3.5 ml, 22 mmol), in 20 ml of dry methylene chloride was added dropwise over a period of 10 minutes. The reaction mixture was stirred in the cold for 2 hours, then cooled further to about −35° C. and treated with isobutanol (dried over 3A molecular sieves), 6.0 gm (7.4 ml, 80 mmol). A stream and dry hydrogen chloride was then passed through the reaction mixture for about 30 seconds. The reaction mixture was refrigerated overnight. Twenty ml of water was then added to the methylene chloride solution. The resulting 2-phase mixture was stirred vigorously for 5 minutes. The methylene chloride layer was separated and washed with 20 ml of water. The aqueous layer and the aqueous wash were combined, washed with ethyl acetate and then adjusted to pH 3.8 with saturated ammonium bicarbonate solution. After 30 minutes at ice bath temperature the aqueous slurry was filtered to provide 1.5 gm (vacuum dried, 83%) of 7-ACA.

(B) Cephalosporin C, sodium salt, dihydrate, 4.8 gm (10 mmol), was suspended in 80 ml of tetrahydrofuran (dried over 5A molecular sieves). Diethyl aniline (dried over KOH), 7.4 gm (8.0 ml, 50 mmol), and acetyl chloride, 4.7 gm (4.3 ml, 60 mmol), were added. The mixture was stirred in a water bath at about 30° to 40° C. for 1 hour and then at room temperature for about 2.5 hours. Filtration removed 5.7 gm of undissolved material. The reaction solution was cooled in an ice-alcohol bath before addition to a solution of the triphenyl phosphite-chlorine complex prepared as in Paragraph A above, but using tetrahydrofuran as a solvent instead methylene chloride. After mixing the two solutions, a solution of diethylaniline, 3.3 gm (22 mmol) in 20 ml of dry tetrahydrofuran, was added dropwise over a period of 10 minutes. The reaction mixture was stirred in the cold for 2 hours, cooled further to about −35° C., and then treated with 16 ml of propylene glycol. A stream of dry hydrogen chloride was passed through the reaction for about 15 seconds. The reaction solution was refrigerated overnight. Workup as described in Paragraph A immediately hereinabove yielded 1.2 gm (45%) of 7-ACA.

(C) N-Chloroacetyl Cephalosporin C, quinoline salt, monohydrate, 3.3 gm (5 mmol), was suspended in 40 ml of methylene chloride (cyclohexane stabilized, dried over 4A molecular sieves). Diethylaniline (dried over KOH), 3.0 gm (20 mmol), and acetyl chloride, 1.9 gm (1.8 ml, 25 mmol), were added. The mixture was stirred at room temperature for 1 hour. The reaction solution was cooled in an ice-alcohol bath before addition to the triphenyl phosphite-chlorine complex, a solution of which was prepared as in Paragraph A immediately hereinabove using 3.4 gm (11 mmol) of triphenyl phosphite.

After mixing the two solutions described in the foregoing paragraph, a solution of diethylaniline, 1.6 gm (11 mmol), in 10 ml of dry methylene chloride was added dropwise over a period of 10 minutes. The reaction was stirred in the cold for 2 hours and then cooled further to about −35° C. and treated with 3.7 ml of isobutanol (dried over 3A molecular sieves). A stream of hydrogen chloride was passed through the reaction solution for about 15 seconds. The reaction mixture was then refrigerated overnight. Following the workup procedure described in Paragraph A immediately hereinabove 730 mg (54%) of 7-ACA was isolated.

EXAMPLE 20

2′,2′,2′-Trichloroethyl 7-amino-3-methyl-3-cephem-4-carboxylate, hydrochloride, in benzene (A) Chlorine gas and 3.16 ml (12 mmol) of triphenyl phosphite were added simultaneously to 45 ml of benzene at 10° to 15° C. A slight yellow color was maintained in the reaction mixture until the last drop of phosphite added cleared the solution. To this solution was added 4.64 gm (10 mmol) of 2′,2′,2′-trichloroethyl 7-phenylacetamido-3-methyl-3-cephem-4-carboxylate. After stirring the reaction mixture for 5 minutes at 10° to 15° C. a solution of 1.1 ml (12.5 mmol) of pyridine in 8 ml of benzene was added over 15 minutes. After stirring the reaction mixture for a total of 45 minutes, 5.1 ml (55 mmol) of isobutanol was added, and HCl was bubbled into the reaction mixture for about 90 seconds. The title product crystallized while the reaction mixture was stirred at room temperature for a period of 2 hours. Filtration provided 3.5 gm (91.6%) of titled nucleus ester hydrochloride: m.p. 179° C. (dec.).

nmr (DMSO d-6) δ2.27 (s, 3), 3.6 (ABq, 2 J=16 Hz), 5.00 (s, 2), and 5.12 (q, 2, J=4 Hz, β-lactam H).

(B) The same procedure was followed as described in Example 20 Paragraph A immediately hereinabove except that all preparations were conducted as room temperature (20°–25° C.) instead of 10°–15° C. A total of 3.26 gm (85.4%) of the title nucleus ester hydrochloride was isolated: m.p. 179° C. (dec.).

EXAMPLE 21

4′-Nitrobenzyl 7-amino-3-chloro-3-cephem-4-carboxylate hydrochloride.

Chlorine gas was bubbled into a solution of 2.63 ml (10 mmol) of triphenyl phosphite in 50 ml of methylene chloride at 0° to 5° C. until a yellow color was obtained. The excess chlorine, evidenced by the yellow color of the solution, was dissipated by adding triphenyl phosphite dropwise until the yellow color was discharged. This required an additional 0.47 ml (1.8 mmol) giving a solution of 11.8 mmol of the triphenyl phosphite-chlorine kinetic compound. To this solution were added 5.04 gm (10 mmol) of 4-nitrobenzyl 7-phenoxyacetamido-3-chloro-3-cephem-4-carboxylate and a solution of 1.01 ml (12.5 mmol) of pyridine in 2 ml of methylene chloride. With the addition of the pyridine solution the temperature of the reaction mixture rose from 5° to 12° C. The solution was then allowed to stir at room temperature for 2 hours after which time was added 5.1 ml (55 mmol) of isobutanol. Within 10 minutes the title nucleus ester hydrochloride began to crystallize from the reaction mixture. After 1½ hours the mixture was filtered to provide, after drying, 3.71 gm (91.4%) of the title product as nearly white crystals: m.p. 180°–181° C. (dec.).

nmr (DMSO d-6) δ3.7 (bs, 2), 5.33 (q, 2, β-lactam H), 5.46 (s, 2), and 7.5–8.4 (ArH).

EXAMPLE 22

4'-Nitrobenzyl
7-amino-3-chloro-3-cephem-4-carboxylate,
hydrochloride.

Chlorine gas was added to a solution of 2.89 ml (11 mmol) of triphenyl phosphite in 50 ml of methylene chloride at 0° to 5° C. until a yellow color persisted in the reaction mixture. Then an additional 0.17 ml (0.65 mmol) of triphenyl phosphite was added to discharge the yellow color. To the resulting solution at 0° to 5° C. were added 4.84 gm (10 mmol) of 4'-nitrobenzyl 7-phenoxyacetamido-3-methyl-3-cephem-4-carboxylate which was washed into the reaction mixture with 5 ml of methylene chloride. Then 1.01 ml (12.5 mmol) of pyridine were added to the reaction mixture resulting in an increase in the temperature from 5° to 10° C. The mixture was then allowed to warm to room temperature and to stir for 2 hours after which time was added 5.1 ml (55 mmol) of isobutanol alcohol. After about 20 minutes a trace of HCl was bubbled into the reaction mixture. The product began to crystallize immediately. After 2.5 hours the reaction mixture was filtered to provide after drying 3.29 gm (85.3%) of the title nucleus ester hydrochloride: m.p. 177° C. (dec.).

An additional 0.32 grams of the title product were isolated after treatment of the filtrate from above with additional HCl gas. Total yield of the title product was 93%.

EXAMPLE 23

4'-Nitrobenzyl
7-amino-3-methyl-3-cephem-4-carboxylate,
hydrochloride.

Chlorine gas was bubbled into a solution of 2.89 ml (11 mmol) of triphenyl phosphite in 50 ml of methylene chloride and 5° to 10° C. until the solution became a pale yellow color indicating excess chlorine. Two drops of triphenyl phosphite were added to discharge the color. To the resulting solution at 5° to 10° C. was added 4.67 gm (10 mmol) of 4'-nitrobenzyl 7-phenylacetamido-3-methyl-3-cephem-4-carboxylate followed by 0.85 ml (10.5 mmol) of pyridine. The solution was then allowed to warm to room temperature. After 2 hours the mixture was cooled to 15° C. before 5.1 ml (55 mmol) of isobutanol was added. The reaction mixture was then stirred for 2 hours at room temperature during which time the product crystallized. Filtration provided, in 3 crops, a total of 3.5 gm (90.6%) of the title nucleus ester hydrochloride: m.p. 188° C. (dec.).

EXAMPLE 24

4'-Nitrobenzyl
7-amino-3-methyl-2-cephem-4-carboxylate,
hydrochloride.

The same procedure was followed as described in Example 23 above except that 4'-nitrobenzyl 7-phenoxyacetamido-3-methyl-2-cephem-4-carboxylate, 4.84 gm (10 mmol), was substituted as the substrate. A total of 3.27 gm (84.7%) of the title nucleus ester hydrochloride were isolated: m.p. 184° C. (dec.).

nmr (DMSO d-6) δ1.96 (s, ), 5.12 (bs, 2), 5.4 (m), 6.34 (bs, 1), and 7.6–8.4 (ArH).

EXAMPLE 25

4'-Nitrobenzyl
7-amino-3-methylenecephem-4-carboxylate,
hydrochloride.

The same procedure was followed as described in Example 23 above except 4'-nitrobenzyl 7-phenoxyacetamido-3-methylenecephem-4-carboxylate 4.83 gm (10 mmol), was used as the substrate. A total of 3.58 gm (92.8%) of titled nucleus ester hydrochloride were isolated: m.p. 176.5°–177° C. (dec.). The nmr spectrum of the product was identical to that described for the product in Example 9 above.

EXAMPLE 26

4'-Nitrobenzyl
7-amino-3-acetoxy-3-cephem-4-carboxylate,
hydrochloride.

Chlorine gas was bubbled through a solution of 2.89 ml (11 mmol) of triphenyl phosphite in 50 ml of methylene chloride at 5° to 10° C. until the yellow color of chlorine persisted. The color was then discharged by the addition of 3 drops of triphenyl phosphite. The cooling bath was removed before 5.28 gm (10 mmol) of 4'-nitrobenzyl 7-phenoxyacetamido-3-acetoxy-3-cephem-4-carboxylate and 0.85 ml (10.5 mmol) of pyridine were added. The reaction was then stirred at room temperature for 2 hours after which time 6.0 ml (64.8 mmol) of isobutanol was added. Within 8 minutes the product began crystallizing from the reaction mixture. After 2 hours the mixture was filtered to provide 2.57 gm (59.9%) of the title nucleus ester hydrochloride as bright white crystals: m.p. −160° C. (dec.). Additional product was noted in the filtrate but no attempt was made to isolate that material.

nmr (DMSO d-6) δ2.2 (s, 3), 3.93 (bs, 2), 5.45 (m) and 7.6–8.4 (ArH).

EXAMPLE 27

4'-Nitrobenzyl
7-amino-3-methyl-3-cephem-4-carboxylate
hydrochloride using
tri(p-chlorophenyl)phosphite-chlorine kinetic complex.

To 5.17 gm (12.5 mmol) of tri(p-chlorophenyl)-phosphite and 0.27 ml (3.28 mmol) of pyridine in 25 ml of methylene chloride at −70° C. was added chlorine gas. Amylene (0.40 ml) was added to discharge excess chlorine. To the resulting solution were added 4'-nitrobenzyl 7-phenoxyacetamido-3-methyl-3-cephem-4-carboxylate (2.42 gm, 5 mmol) and pyridine (0.79 ml, 9.22 mmol) in 4 ml of methylene chloride dropwise over 11 minutes. After 3 hours the cooling bath was removed and 6.94 ml of isobutanol was added. After the reaction mixture had warmed to about −10° C. HCl gas was bubbled into the mixture for about 1 minute. After 15 minutes the reaction mixture was filtered to give 1.86 gm (96%) of the titled product as a white solid. m.p. 184°–185° C. (dec.).

EXAMPLE 28

Benzyl 7-(1-chloro-2-phenylethylidene)-7-methoxy-3-acetoxymethyl-3-cephem-4-carboxylate.

To a solution of the triphenyl phosphite-chlorine complex prepared from chlorine and 12.3 mmol of triphenyl phosphite in the presence of 0.1 ml of pyridine in 45 ml of methylene chloride at −15° C., was added 5.11 gm (10 mmol) of benzyl 7-phenylacetamido-7-methoxy-3-acetoxymethyl-3-cephem-4-carboxylate and dropwise over 10 minutes a solution of 1.01 ml (12.5 mmol) of pyridine in 4 ml of methylene chloride. After 50 minutes at −15° to −10° C., 2.1 ml (30 mmol) of propylene oxide. After and additional 10 minutes (reaction temperature to 0° C.), the reaction mixture was washed with 25 ml of ice water, dried over $CaCl_2$ and evaporated in vacuo to 11 gm of syrup. The product was triturated 3 times under carbon tetrachloride and then taken up in 50 ml of ether. The etheral solution was decanted from 0.5 gm of precipitate and then evaporated in vacuo to about 25 ml. An oily product was obtained with the resulting etheral solution was diluted with 25 ml of hexane. The oil was washed twice with 1:1/hexane:ether and then evaporated in vacuo to a foam twice from carbon tetrachloride solutions to provide 2.5 gm of the title product:

ir ($CHCl_3$) 1780 and 1730 cm$^{-1}$. nmr ($CDCl_3$, pyridine d-5) δ1.96 (s, 3), 3.3 (ABq), 3.43 (s, 2), 3.93 (s, 2), 4.86 (ABq), 4.93 (s, 1), 5.25 (s, 1) and 7.3 (ArH).

EXAMPLE 29

4'-Nitrobenzyl 7-amino-3-methyl-3-cephem-4-carboxylate hydrobromide.

To a solution of 25.4 ml of triphenylphosphite-bromine complex prepared by reacting 6.67 ml (25.4 mmol) of triphenyl phosphite and 1.30 ml (25.4 mmol) of bromine in the presence of 2.10 ml (26 mmol) of pyridine in 100 ml of methylene chloride at −10° to −15° C. was added 4'-nitrobenzyl 7-phenoxyacetamido-3-methyl-3-cephem-4-carboxylate (9.67 gm, 20 mmol). After 1 hour at −10° to −15° C., the reaction mixture was removed from the cooling bath. Isobutanol (13.88 ml. 150 mmol) was added. After stirring for 2 hours at room temperature the reaction mixture was filtered to provide 4.76 gm (55.3%) of the titled product. m.p. 179°–181° C. (dec.).

Anal calcd for $C_{15}H_{16}N_3O_5SBr$: C, 41.87; H, 3.75; N, 9.77; S, 7.45; Br, 18.57. Found: C, 42.04; H, 3.57; N, 9.54; S, 7.54; Br, 18.37. nmr (DMSO d-6) δ2.2 (s, 3), 3.65 (bs, 2), 5.27 (m, 2, β-lactam-H), 5.42 (s, 2), and 7.6–8.4 (m, 4, ArH).

EXAMPLE 30

Benzhydryl 7-(α-chloro-4-methylbenzylidenimino)-7-methoxy-3-(1-methyl-1,2,3,4-tetrazol-5-ylthio)methyl-1-dethia-1-oxa-3-cephem-4-carboxylate.

To a solution of 200 mg of benzhydryl 7-(4-methylbenzamido)-7-methoxy-3-(1-methyl-1,2,3,4-tetrazol-5-ylthio)methyl-1-dethia-1-oxa-3-cephem-4-carboxylate in 10 ml of deuterochloroform at 0° to −15° C. was added, over a period of several hours, 4 equivalents of triphenyl phosphite-chlorine complex (prepared in usual manner) and 4 equivalents of pyridine. The large excess of the complex and pyridine was required probably because of impurities in the oxa cephem starting material. Precipitation of salts and impurities with $CCl_4$ and then with ether give oils on evaporation of the solvent. A nmr spectrum of the oil from the ether extract showed signals for triphenyl phosphite in addition to those for the title product.

nmr ($CDCl_3$) δ2.25 (s, 3), 3.53 (s, 3), 3.65 (s, 3), 4.16 (s, 2), 4.53 (bs, 2) and 5.16 (s, 1, C-6 H).

We claim:

1. A process for preparing penicillin or cephalosporin imino halides which comprises reacting a C-6 acylamino penicillin or a C-7 acylamino cephalosporin with about 1.0 to about 2.0 equivalents of a halogenating compound of the formula

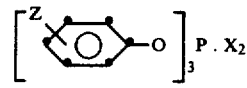

wherein X is Cl or Br, and Z is hydrogen, halo, $C_1$–$C_4$ alkyl or $C_1$–$C_4$ alkoxy, which is the kinetically controlled product of the reaction of equivalent amounts of a triaryl phosphite of the formula

and chlorine or bromine in an inert organic solvent, in the presence of about 1.0 to about 1.2 equivalents of a tertiary amine base per equivalent of halogenating compound employed, in a substantially anhydrous inert organic solvent at a temperature of about 30° C. or below, with the proviso that when the C-6 acylamino penicillin or C-7 acylamino cephalosporin is substituted by hydroxy, amino or carboxy groups those groups are first protected with conventional hydroxy, amino or carboxy protecting groups.

2. The process of claim 1 wherein X is Cl.
3. The process of claim 1 wherein Z is hydrogen.
4. The process of claim 1 wherein X is Br.
5. The process of claim 4 wherein Z is hydrogen.
6. The process of claim 1 wherein X is Cl and Z is hydrogen.
7. A process for preparing penicillin or cephalosporin imino chlorides which comprises reacting a C-6 acylamino penicillin or a C-7 acylamino cephalosporin with about 1.0 to about 2.0 equivalents of a chlorinating compound of the formula

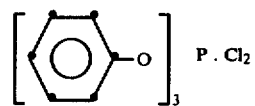

which
(a) has a $^{31}P$ nuclear magnetic resonance signal in methylene chloride at −3.7 ppm relative to that of phosphoric acid;

(b) has in methylene chloride an infrared spectrum which has the following characteristic absorptions: 1120–1190 (very strong), 1070 (very strong), 1035 (strong), 1010 (very strong), 990 (very strong), 640 (medium), 625 (medium), 580 (weak), 510 (strong) and 465 (weak);

(c) reacts with water to give HCl and triphenyl phosphate; and (d) reacts with n-butanol to give HCl, n-butyl chloride, and triphenyl phosphate;

in the presence of about 1.0 to about 1.2 equivalents of a tertiary amine base per equivalent of chlorinating compound employed, in a substantially anhydrous inert organic solvent at a temperature of about 30° C. or below, with the proviso that when the C-6 acylamino penicillin or C-7 acylamino cephalosporin is substituted by hydroxy, amino or carboxy groups, those groups are first protected with conventional hydroxy, amino, or carboxy protecting groups.

8. The process of claim 1 or claim 7 wherein the C-6 acylamino penicillin or C-7 acylamino cephalosporin is a compound of the formula

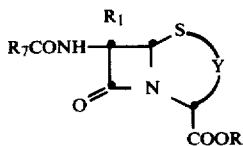

wherein

R is a carboxylic acid protecting group;

$R^1$ is hydrogen or methoxy;

$R_7CO-$ is an acyl group derived from a carboxylic acid; and

Y is divalent radical selected from the group consisting of

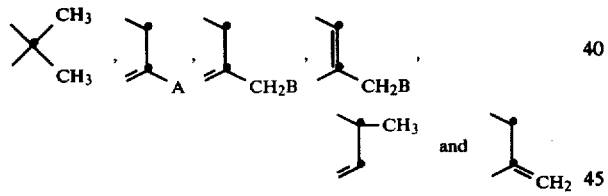

wherein A is hydrogen, chloro, bromo, protected hydroxy, $C_1$–$C_4$ alkoxy, methyl, $C_1$–$C_4$ alkanesulfonyloxy or $C_1$–$C_4$ alkylphenylsulfonyloxy; and B is (1) $C_2$–$C_4$ alkanoyl, carbamoyloxy, or $C_1$–$C_5$ alkycarbamoyloxy;

(2) $C_1$–$C_4$ alkoxy;

(3) chloro or bromo;

(4) a group of the formula -$SR_9$ wherein $R_9$ is (a) $C_1$–$C_4$ alkanoyl;

(b) $C_1$–$C_4$ alkyl, phenyl or phenyl substituted with 1 or 2 substituents selected from the group consisting of $C_1$–$C_4$ alkyl, $C_1$–$C_4$ alkoxy, protected hydroxy, chloro, bromo, fluoro, nitro, cyano, methanesulfonamido and trifluoromethyl; or (c) a 5- or 6-membered heterocyclic ring containing 1 to 4 heteroatoms selected from the group consisting of oxygen, sulfur and nitrogen, said ring being unsubstituted or substituted by $C_1$–$C_4$ alkyl, $C_1$–$C_4$ alkoxy, chloro, bromo, oxo, halo($C_1$–$C_4$ alkyl), protected amino, protected amino($C_1$–$C_4$ alkyl), protected hydroxy, protected hydroxy ($C_1$–$C_4$ alkyl), protected carboxy, or protected carboxy ($C_1$–$C_4$ alkyl).

9. The process of claim 8 wherein $R_1$ is hydrogen.

10. The process of claim 1 or claim 7 wherein the C-7 acylamino cephalosporin is a compound of the formula

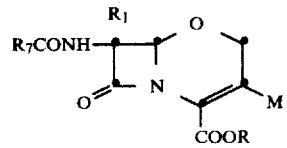

wherein

R is a carboxylic acid protecting group;

$R_1$ is hydrogen or methoxy;

$R_7CO-$ is an acyl group derived from a carboxylic acid; and

M is hydrogen, chloro, bromo, protected hydroxy, $C_1$–$C_4$ alkoxy, methyl, $C_1$–$C_4$ alkylphenylsulfonyloxy, or a group of the formula —$CH_2B$ wherein B is (1) $C_2$–$C_4$ alkanoyl, carbamoyloxy, or $C_1$–$C_4$ alkylcarbamoyloxy;

(2) $C_1$–$C_4$ alkoxy;

(3) chloro or bromo;

(4) a group of the formula —$SR_9$ wherein $R_9$ is (a) $C_1$–$C_4$ alkanoyl;

(b) $C_1$–$C_4$ alkyl, phenyl or phenyl substituted with 1 or 2 substituents selected from the group consisting of $C_1$–$C_4$ alkyl, $C_1$–$C_4$ alkoxy, protected hydroxy, chloro, bromo, fluoro, nitro, cyano, methanesulfonamido and trifluoromethyl; or (c) a 5- or 6-membered heterocyclic ring containing 1 to 4 heteroatoms selected from the group consisting of oxygen, sulfur and nitrogen, said ring being unsubstituted or substituted by $C_1$–$C_4$ alkyl, $C_1$–$C_4$ alkoxy, chloro, bromo, oxo, halo ($C_1$–$C_4$ alkyl), protected amino, protected amino($C_1$–$C_4$ alkyl), protected hydroxy, protected hydroxy ($C_1$–$C_4$ alkyl), protected carboxy, or protected carboxy-($C_1$–$C_4$ alkyl).

11. The process of claim 10 wherein $R_1$ is hydrogen.

12. The process of claim 6 or claim 7 wherein the tertiary amine base has a $pK_b$ value of about 6 to about 10.

13. The process of claim 12 wherein about 1.1 to about 1.2 equivalents of halogenating compound are employed for each equivalent of C-6 acylamino penicillin or C-7 acylamino cephalosporin starting material.

14. The process of claim 13 wherein Y is a group of the formula

15. The process of claim 13 wherein after formation of the imino chloride product an excess of a $C_1$–$C_{15}$ aliphatic alcohol and hydrogen chloride is added to the reaction mixture to provide the corresponding 6-aminopenicillin or 7-aminocephalosporin.

16. The process of claim 14 wherein about one equivalent of tertiary amine base is employed for each equivalent of halogenating compound employed.

17. The process of claim 16 wherein the temperature is about 0° or below.

18. The process of claim 17 wherein after formation of the imino chloride product is complete an excess of a $C_1$–$C_{15}$ aliphatic alcohol and hydrogen chloride is added to the reaction product mixture to provide the corresponding C-7 aminocephalosporin.

19. The process of claim 18 wherein about a 3–6 fold excess of a $C_4$–$C_{12}$ β-disubstituted primary aliphatic alcohol or about a 2–3 fold excess of a $C_3$–$C_{15}$ aliphatic 1,3-diol or a $C_2$–$C_{12}$ aliphatic 1,2-diol is added to the reaction product mixture after imino chloride formation is complete.

20. The process of claim 19 wherein the halogenation is carried out at a temperature of about −70° to about 0° C.

21. The process of claim 20 wherein the alcohol is diol employed is isobutanol, 1,3-propandiol, or 1,2-propanediol.

22. The process of claim 20 wherein the inert organic solvent is an aromatic hydrocarbon or a halogenated hydrocarbon.

23. The process of claim 22 wherein a 7-acylamino cephalosporin is employed and the acylamino group is selected from phenylacetamido, phenoxyacetamido, heptanoylamino, 4-protected amino-4-protected carboxybutyramido, benzamido, and 2-thienylacetamido.

24. The process of claim 23 wherein the halogenating compound is stabilized by a tertiary amine base.

* * * * *